(12) United States Patent
Helton et al.

(10) Patent No.: US 9,572,721 B2
(45) Date of Patent: Feb. 21, 2017

(54) METHOD FOR MANUFACTURING ABSORBENT ARTICLES INCLUDING A DISCRETE BARRIER MEMBER

(71) Applicant: The Procter & Gamble Company, Cincinnati, OH (US)

(72) Inventors: Ronald Herbert Helton, Cincinnati, OH (US); Darrell Ian Brown, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 82 days.

(21) Appl. No.: 14/723,978

(22) Filed: May 28, 2015

(65) Prior Publication Data

US 2015/0342790 A1 Dec. 3, 2015

Related U.S. Application Data

(60) Provisional application No. 62/004,251, filed on May 29, 2014.

(51) Int. Cl.
*A61F 13/00* (2006.01)
*A61F 13/15* (2006.01)
(Continued)

(52) U.S. Cl.
CPC ... *A61F 13/15682* (2013.01); *A61F 13/15593* (2013.01); *A61F 13/15756* (2013.01);
(Continued)

(58) Field of Classification Search
CPC ........ A61F 13/00; A61F 13/15; A61F 13/156; A61F 13/1568; A61F 13/15682; A61F 13/15593; A61F 13/15756; A61F 13/15804; A61F 13/49; A61F 13/49017; A61F 13/49413; A61F 13/49446; A61F 13/495; A61F 13/49; A61F 13/155; A61F 13/157; A61F 13/158
See application file for complete search history.

(56) References Cited

U.S. PATENT DOCUMENTS 3,848,594 A 11/1974 Buell
3,860,003 A 1/1975 Buell
(Continued)

FOREIGN PATENT DOCUMENTS

EP 0 812 789 A2 12/1997
WO WO 98/53779 A1 12/1998
(Continued)

OTHER PUBLICATIONS

U.S. Appl. No. 14/572,861, filed Dec. 14, 2014, Martynus.
(Continued)

*Primary Examiner* — Michael N Orlando
*Assistant Examiner* — Matthew Hoover
(74) *Attorney, Agent, or Firm* — Sarah M. DeCristofaro

(57) ABSTRACT

A method for manufacturing an absorbent article including a topsheet, a backsheet, a core, a discrete barrier member, a first cuff, and a second cuff. A barrier substrate may be cut into a discrete barrier member including a leading edge portion, an opposing trailing edge portion, and a central portion therebetween. The discrete barrier substrate may be transferred onto a folding roll. A first cuff substrate and a second cuff substrate may be advanced onto the folding roll such that the discrete barrier substrate may be disposed on at least a portion of the first cuff substrate and the second cuff substrate. The discrete barrier member may include a fold between the leading edge portion and the trailing edge portion. A topsheet substrate may associate with at least a portion of the discrete barrier member, the first cuff substrate, and the second cuff substrate.

20 Claims, 20 Drawing Sheets

(51) Int. Cl.
  *A61F 13/49* (2006.01)
  *A61F 13/494* (2006.01)
  *A61F 13/495* (2006.01)

(52) U.S. Cl.
  CPC ...... *A61F 13/15804* (2013.01); *A61F 13/495* (2013.01); *A61F 13/49017* (2013.01); *A61F 13/49413* (2013.01); *A61F 13/49446* (2013.01); *A61F 2013/4951* (2013.01); *A61F 2013/4953* (2013.01); *A61F 2013/4956* (2013.01); *Y10T 156/1015* (2015.01)

(56) References Cited

U.S. PATENT DOCUMENTS

| | | | |
|---|---|---|---|
| 3,905,592 A | 9/1975 | Spencer et al. | |
| 4,610,678 A | 9/1986 | Weisman et al. | |
| 4,662,875 A | 5/1987 | Hirotsu et al. | |
| 4,673,402 A | 6/1987 | Weisman et al. | |
| 4,695,278 A | 9/1987 | Lawson | |
| 4,704,115 A | 11/1987 | Buell | |
| 4,795,454 A | 1/1989 | Dragoo | |
| 4,834,735 A | 5/1989 | Alemany et al. | |
| 4,846,815 A | 7/1989 | Scripps | |
| 4,854,984 A | 8/1989 | Ball et al. | |
| 4,888,231 A | 12/1989 | Angstadt | |
| 4,894,060 A | 1/1990 | Nestegard | |
| 4,909,803 A | 3/1990 | Aziz et al. | |
| 4,919,738 A | 4/1990 | Ball et al. | |
| 4,946,527 A | 8/1990 | Battrell | |
| 5,151,092 A | 9/1992 | Buell et al. | |
| 5,221,274 A | 6/1993 | Buell et al. | |
| 5,562,646 A | 10/1996 | Goldman et al. | |
| 5,599,335 A | 2/1997 | Goldman et al. | |
| 5,628,097 A | 5/1997 | Benson et al. | |
| 5,669,894 A | 9/1997 | Goldman et al. | |
| 5,693,165 A | 12/1997 | Schmitz | |
| 5,702,551 A | 12/1997 | Huber et al. | |
| 5,711,847 A | 1/1998 | Rajala et al. | |
| 5,817,199 A | 10/1998 | Brennecke et al. | |
| 5,916,661 A | 6/1999 | Benson et al. | |
| 6,107,539 A | 8/2000 | Palumbo et al. | |
| 6,123,792 A | 9/2000 | Samida et al. | |
| 6,248,195 B1 | 6/2001 | Schmitz | |
| 6,349,867 B1 | 2/2002 | Fernfors | |
| 6,409,711 B1* | 6/2002 | Jonbrink | A61F 13/495 604/378 |
| 6,450,321 B1 | 9/2002 | Blumenthal et al. | |
| 6,545,197 B1 | 4/2003 | Muller et al. | |
| 6,546,987 B1 | 4/2003 | Tachibana et al. | |
| 6,596,108 B2 | 7/2003 | McCabe | |
| 6,632,504 B1 | 10/2003 | Gillespie et al. | |
| 6,705,453 B2 | 3/2004 | Blumenthal et al. | |
| 6,790,798 B1 | 9/2004 | Suzuki et al. | |
| 6,811,019 B2 | 11/2004 | Christian et al. | |
| 6,814,217 B2 | 11/2004 | Blumenthal et al. | |
| 7,449,084 B2 | 11/2008 | Nakakado | |
| 7,569,039 B2 | 8/2009 | Matsuda et al. | |
| 8,377,249 B2 | 2/2013 | Gill | |
| 8,752,300 B2 | 6/2014 | Masek et al. | |
| 2003/0021651 A1 | 1/2003 | Suzuki et al. | |
| 2004/0097895 A1 | 5/2004 | Busam et al. | |
| 2004/0158212 A1 | 8/2004 | Ponomarenko et al. | |
| 2005/0038401 A1* | 2/2005 | Suzuki | A61F 13/495 604/385.01 |
| 2005/0107764 A1 | 5/2005 | Matsuda et al. | |
| 2007/0156110 A1* | 7/2007 | Thyfault | A61F 13/495 604/385.101 |
| 2009/0312730 A1 | 12/2009 | LaVon et al. | |
| 2012/0015791 A1 | 1/2012 | Yamamoto | |
| 2012/0061015 A1 | 3/2012 | LaVon et al. | |
| 2012/0061016 A1 | 3/2012 | LaVon et al. | |
| 2012/0152695 A1 | 6/2012 | Coenen et al. | |
| 2013/0255861 A1 | 10/2013 | Schneider | |
| 2013/0255862 A1 | 10/2013 | Schneider et al. | |
| 2013/0255863 A1 | 10/2013 | LaVon et al. | |
| 2013/0255864 A1 | 10/2013 | Schneider et al. | |
| 2013/0255865 A1 | 10/2013 | Brown et al. | |
| 2014/0000794 A1 | 1/2014 | Hamilton et al. | |
| 2014/0000795 A1 | 1/2014 | Hamilton et al. | |
| 2014/0000798 A1 | 1/2014 | Hargett et al. | |
| 2014/0005021 A1 | 1/2014 | Walsh et al. | |
| 2014/0110053 A1 | 4/2014 | Ordway et al. | |
| 2014/0245865 A1 | 9/2014 | Masek et al. | |
| 2014/0336605 A1 | 11/2014 | Hardie et al. | |
| 2014/0377506 A1 | 12/2014 | Bao et al. | |
| 2014/0377513 A1 | 12/2014 | Galie et al. | |
| 2015/0088088 A1 | 3/2015 | Wade et al. | |
| 2015/0209195 A1 | 7/2015 | Martnus et al. | |
| 2015/0223995 A1 | 8/2015 | Martnus et al. | |
| 2015/0223996 A1 | 8/2015 | Martnus et al. | |
| 2015/0257946 A1 | 9/2015 | Martnus et al. | |
| 2015/0284892 A1 | 10/2015 | Galie et al. | |
| 2015/0342791 A1 | 12/2015 | Helton et al. | |

FOREIGN PATENT DOCUMENTS

| | | |
|---|---|---|
| WO | WO 2009/032995 A1 | 3/2009 |
| WO | WO 2014/120872 A1 | 8/2014 |

OTHER PUBLICATIONS

U.S. Appl. No. 14/572,871, filed Dec. 17, 2014, Martynus.
U.S. Appl. No. 14/572,886, filed Dec. 17, 2014, Martynus.
U.S. Appl. No. 14/572,894, filed Dec. 17, 2014, Martynus.
U.S. Appl. No. 14/247,276, filed Apr. 8, 2014, Galie.
U.S. Appl. No. 14/724,028, filed May 28, 2015, Helton.
U.S. Appl. No. 62/129,049, filed Mar. 6, 2015, Brown.
U.S. Appl. No. 62/129,050, filed Mar. 6, 2015, Brown.
13372 PCT International Search Report, dated Sep. 9, 2015, 10 pages.
13373 PCT International Search Report, dated Sep. 9, 2015, 10 pages.

* cited by examiner

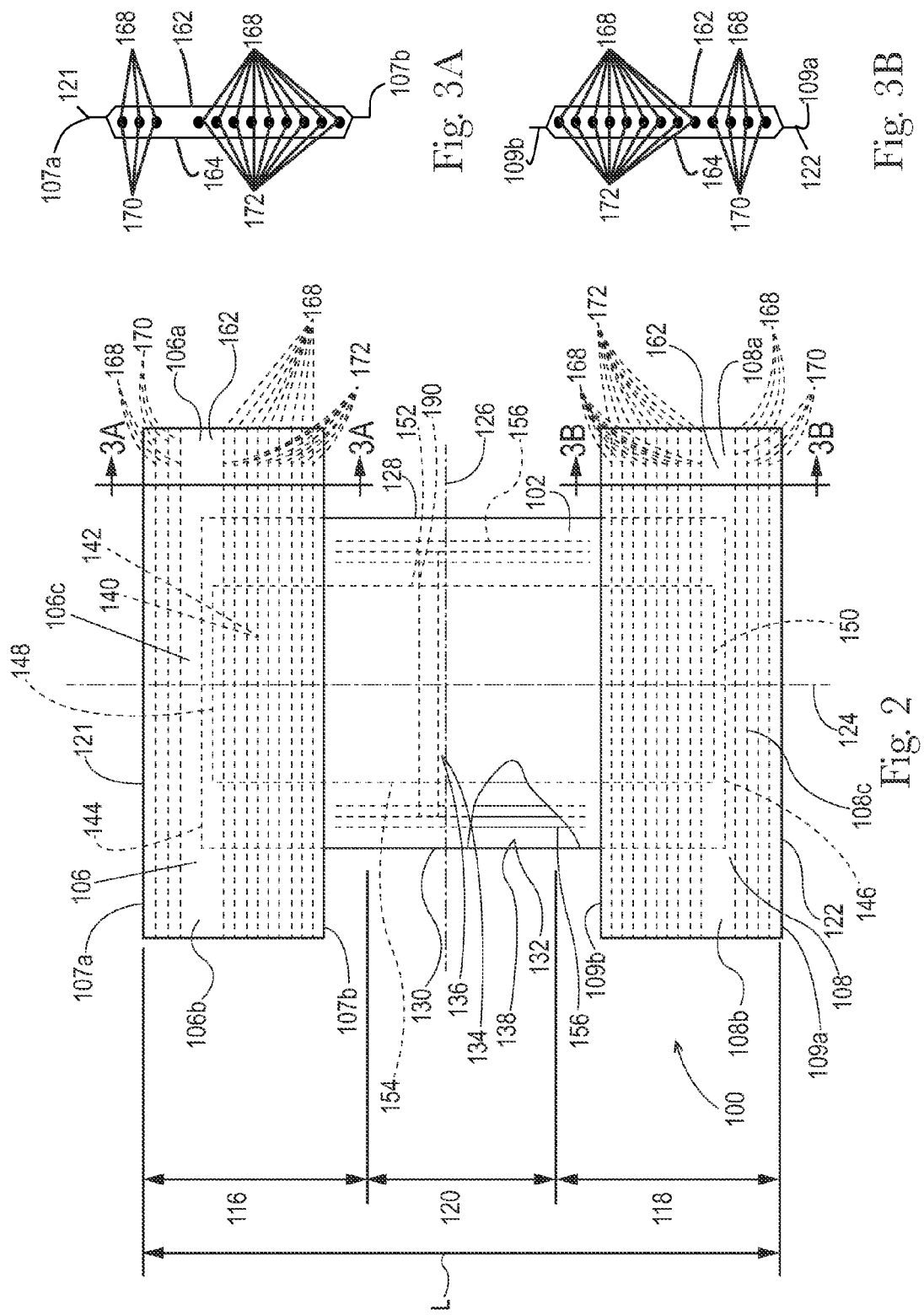

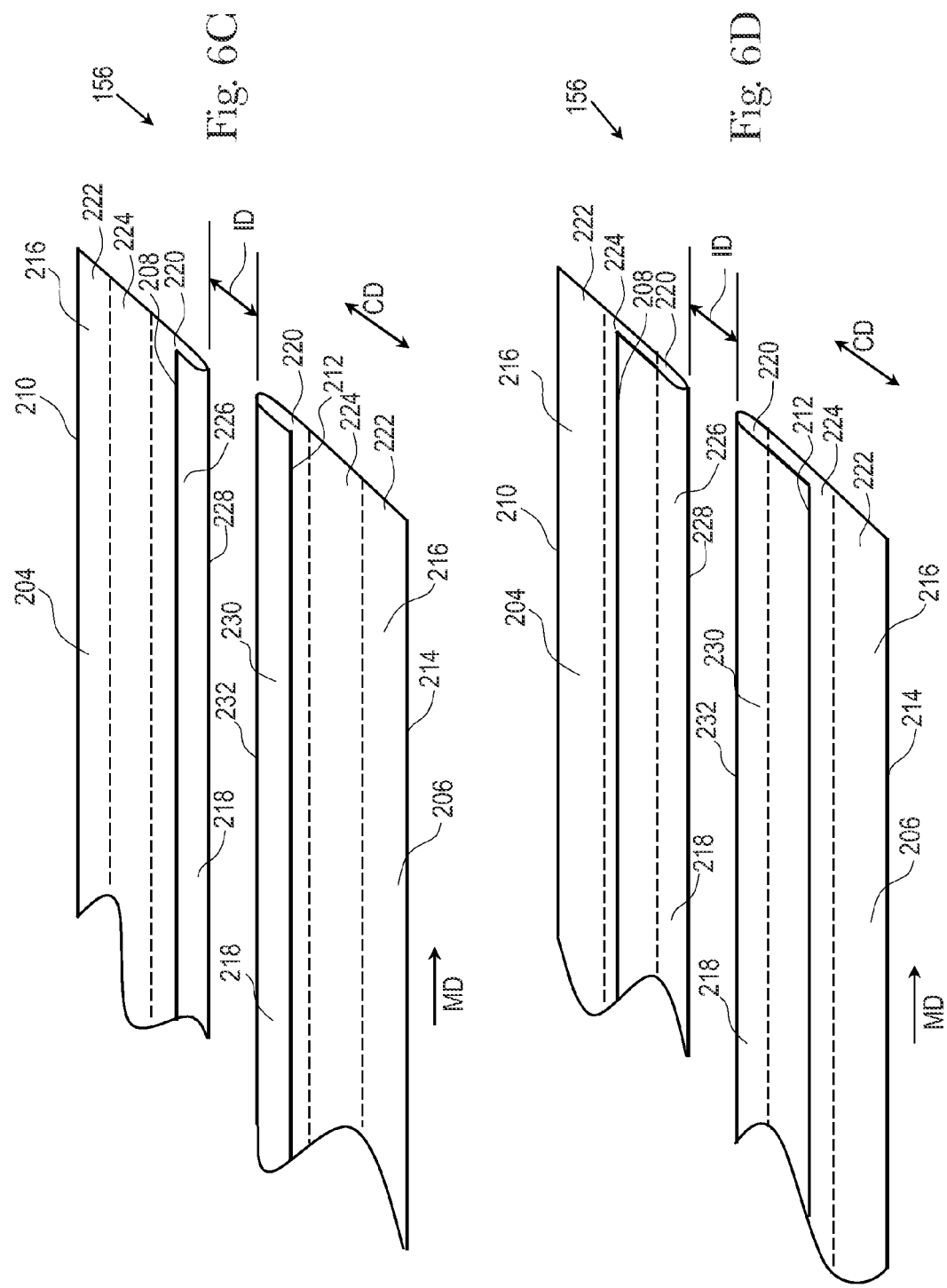

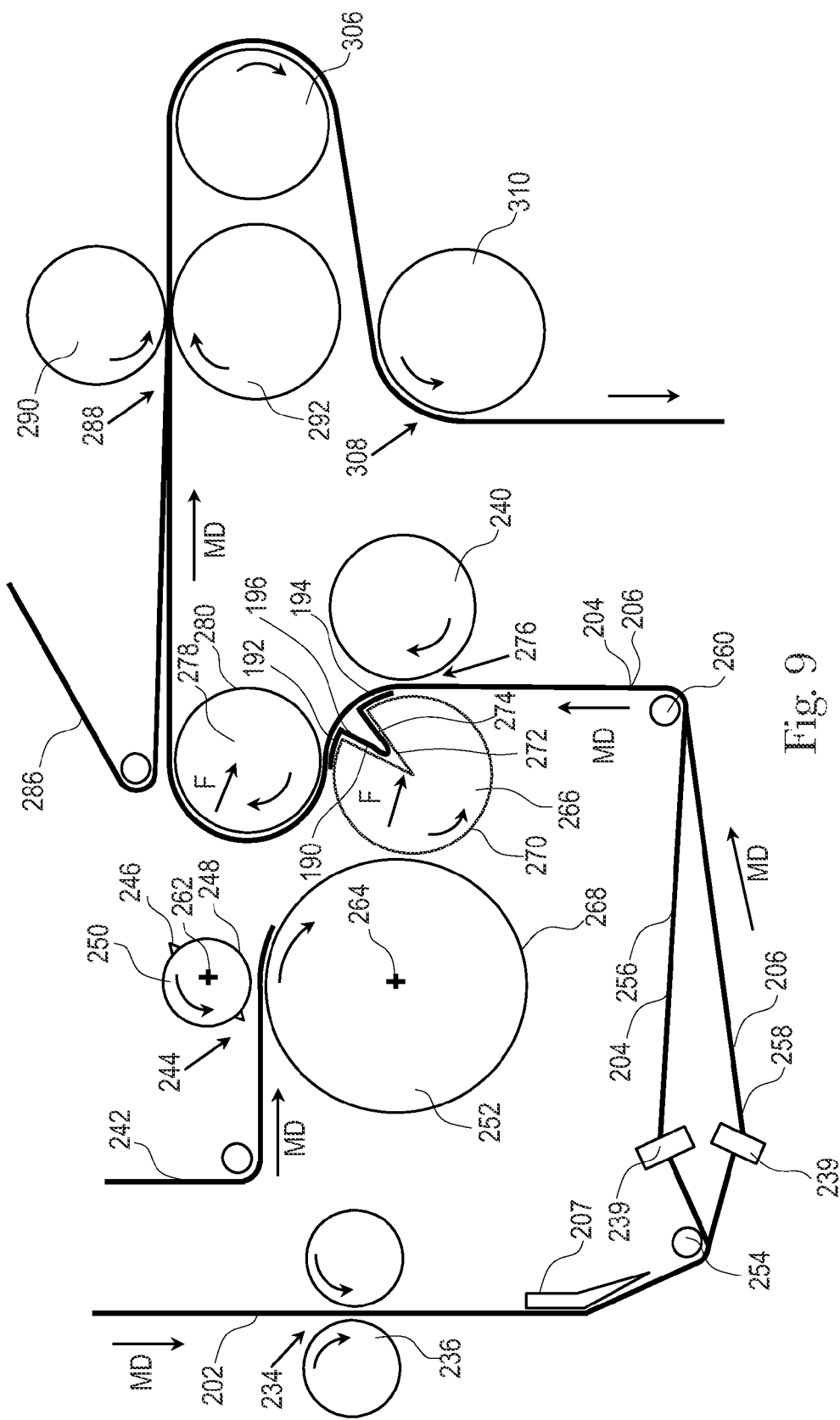

METHOD FOR MANUFACTURING ABSORBENT ARTICLES INCLUDING A DISCRETE BARRIER MEMBER

CROSS REFERENCE TO RELATED APPLICATION

This application claims the benefit of U.S. Provisional Application No. 62/004,251 filed on May 29, 2014, the substance of which is incorporated herein by reference.

FIELD OF THE INVENTION

The present disclosure relates to methods for manufacturing absorbent articles, and more particularly, methods for manufacturing absorbent articles including a discrete barrier member.

BACKGROUND OF THE INVENTION

Along an assembly line, diapers and various types of other absorbent articles may be assembled by adding components to and otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. Webs of material and component parts used to manufacture diapers may include: backsheets, topsheets, absorbent cores, front and/or back ears, fastener components, and various types of webs and components such as leg elastics, barrier leg cuff elastics, and waist elastics. Once the desired component parts are assembled, the advancing web(s) and component parts are subjected to a final knife cut to separate the web(s) into discrete diapers or other absorbent articles. The discrete diapers or absorbent articles may also then be folded and packaged.

As mentioned above, during the assembly process, component parts such as elastics and other materials are used to manufacture diapers. Generally, a number of component parts have been added to absorbent articles to improve the fit of the absorbent article, to reduce leakage of the absorbent article, and to reduce irritation to the skin of the wearer of the absorbent article. To accomplish these objectives, absorbent articles having an opening that provides a passageway to void space for collected feces and urine have been proposed. Similarly, absorbent articles having a barrier member to create separate areas for urine and feces have also been proposed.

However, it has been found that these absorbent articles are expensive to manufacture due to the added number of component parts. For example, elastics and additional nonwoven materials have been added to the absorbent article to create a barrier for feces and urine. Further, these absorbent articles are difficult to manufacture due to the complexity of adding additional component parts to partition the absorbent article while maintaining relatively high manufacturing speeds.

In addition, some absorbent articles that currently provide a means for separating feces and urine are inadequate. For example, it has been found that barrier members may fail to provide the desired tension across the absorbent article to separate bodily exudates. More specifically, once the absorbent article has been placed on the wearer, the barrier members have been found to slump or bunch such that the barrier member loses contact with the wearer and provides an opening to allow feces and urine to move uninhibited throughout the absorbent article.

Thus, a need exists for improved methods of manufacturing absorbent articles including discrete barrier members that separate feces and urine and are more easily maintained in close contact with the wearer's body.

SUMMARY OF THE INVENTION

Aspects of the present disclosure relate to a method for assembling absorbent articles. The method may include the following step. A first cuff substrate and a second cuff substrate may be advanced in a machine direction. The first cuff substrate may include a first inner cuff edge and a first outer cuff edge and the second cuff substrate may include a second inner cuff edge and a second outer cuff edge. The first inner cuff edge may be separated from the second inner cuff edge in a cross direction by a first distance. A discrete barrier member may be advanced in the machine direction. The barrier member may include a leading edge portion, a trailing edge portion opposite the leading edge portion, and a central portion between the leading edge portion and the trailing edge portion. The discrete barrier member may be folded between the leading edge portion and the trailing edge portion. The trailing edge portion of the discrete barrier member may be connected with the first cuff substrate and the second cuff substrate. The trailing edge portion of the discrete barrier member may extend in the cross direction by separating the first cuff substrate and the second cuff substrate such that the first inner cuff edge is separated from the second inner cuff edge in the cross direction by a second distance. The second distance may be greater than the first distance. A topsheet substrate including a first topsheet edge and a second topsheet edge opposite from the first topsheet edge may be advanced in the cross direction. The leading edge portion of the discrete barrier member may be connected with the topsheet substrate.

In another embodiment, a method for manufacturing an absorbent article, wherein the absorbent article comprises a topsheet, a backsheet, a core, a discrete barrier member, a first cuff, and a second cuff may include the following steps. A first cuff substrate and a second cuff substrate may be advanced in a machine direction. The first cuff substrate may include a first inner cuff edge and an opposing first outer cuff edge. The second cuff substrate may include a second inner cuff edge and an opposing second outer cuff edge. Each of the first cuff substrate and the second cuff substrate may include a first cuff surface and a second cuff surface that each include an inner edge region, an opposing outer edge region, and a central region therebetween. The first cuff substrate may be folded such that the first inner cuff edge may be associated with at least one of the first edge region and the central region of the first cuff surface to form a first cuff fold. The first cuff fold may include a first fold edge. The second cuff substrate may be folded such that the second inner cuff edge may be associated with at least one of the first edge region and the central region of the first cuff surface to form a second cuff fold. The second cuff fold may include a second fold edge. The first fold edge may be separated by the second fold edge by a first distance in a cross direction. A discrete barrier member may be advanced in the machine direction. The barrier member may include a leading edge portion, a trailing edge portion opposite the leading edge portion, and a central portion between the leading edge portion and the trailing edge portion. The discreet barrier member may be folded between the leading edge portion and the trailing edge portion. The trailing edge portion of the discrete barrier member may be connected with the first cuff substrate and the second cuff substrate. A topsheet may be advanced in the machine direction. The topsheet substrate may include a first topsheet edge opposite from the second topsheet edge in the cross direction. The first topsheet edge and the second topsheet edge may extend longitudinally in the machine direction. The leading edge portion of the discrete barrier member may be connected with the topsheet substrate.

In yet another embodiment, a method for manufacturing an absorbent article, wherein the absorbent article comprises a topsheet, a backsheet, a core, a discrete barrier member, a first cuff, and a second cuff may include the following steps. A barrier substrate may be cut into a discrete barrier member including a leading edge portion, an opposing trailing edge portion, and a central portion therebetween. The discrete barrier substrate may be transferred onto a folding roll. A first cuff substrate and a second cuff substrate may be advanced onto the folding roll such that the discrete barrier substrate may be disposed on at least a portion of the first cuff substrate and the second cuff substrate. The trailing edge portion of the discrete barrier member may be connected with the first cuff substrate and the second cuff substrate. The discrete barrier member may include a fold between the leading edge portion and the trailing edge portion. A topsheet substrate may associate with at least a portion of the discrete barrier member, the first cuff substrate, and the second cuff substrate. The leading edge portion of the discrete barrier member may be connected with the topsheet substrate.

BRIEF DESCRIPTION OF THE DRAWINGS

FIG. 2 is a partially cut away plan view of the diaper pant shown in FIG. 1;

FIG. 3A is a cross-sectional view of the diaper pant of FIG. 2 taken along line 3A-3A in accordance with one non-limiting embodiment of the present disclosure;

FIG. 3B is a cross-sectional view of the diaper pant of FIG. 2 taken along line 3B-3B in accordance with one non-limiting embodiment of the present disclosure;

FIG. 6C is a perspective view of a first cuff substrate and a second cuff substrate of FIG. 5B taken along line 6C-6C in accordance with one non-limiting embodiment of the present disclosure;

FIG. 6D is a perspective view of a first cuff substrate and a second cuff substrate of FIG. 5B taken along line 6C-6C in accordance with one non-limiting embodiment of the present disclosure;

FIG. 9 is a schematic representation of a process used to manufacture absorbent articles comprising a discrete barrier member in accordance with one non-limiting embodiment of the present disclosure;

DETAILED DESCRIPTION OF THE INVENTION

Figure 1:
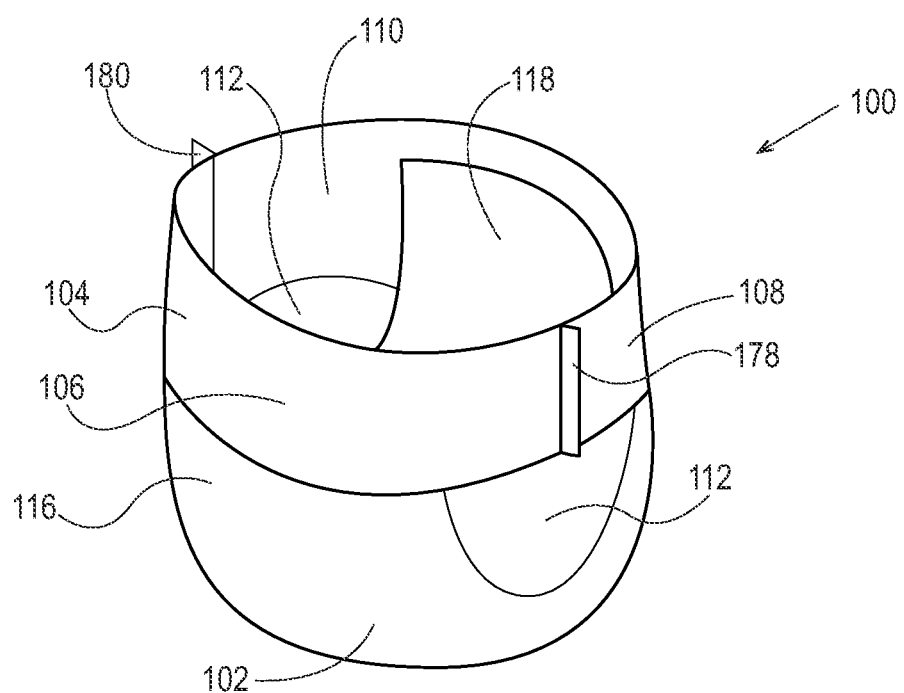
FIG. 1 is a perspective view of a diaper pant.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant may be configured with a continuous or closed waist opening and at least one continuous, closed, leg opening prior to the article being applied to the wearer.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

"Substrate" is used herein to describe a material which is primarily two-dimensional (i.e. in an XY plane) and whose thickness (in a Z direction) is relatively small (i.e. 1/10 or less) in comparison to the substrate's length (in an X direction) and width (in a Y direction). Non-limiting examples of substrates include a web, layer or layers or fibrous materials, nonwovens, films and foils such as polymeric films or metallic foils. These materials may be used alone or may comprise two or more layers joined together. As such, a web is a substrate.

"Nonwoven" refers herein to a material made from continuous (long) filaments (fibers) and/or discontinuous (short) filaments (fibers) by processes such as spunbonding, melt-blowing, carding, and the like. Nonwovens do not have a woven or knitted filament pattern.

The term "machine direction" (MD) is used herein to refer to the direction of material flow through a process. In addition, relative placement and movement of material may be described as flowing in the machine direction through a process from upstream in the process to downstream in the process.

The term "cross direction" (CD) is used to herein refer to the direction perpendicular to the direction of material flow through a process. The cross direction may be substantially perpendicular to the machine direction.

The present disclosure relates to methods for manufacturing absorbent articles including a discrete barrier member. More particularly, the methods are directed to manufacturing an absorbent article including a topsheet, a backsheet, a core, a discrete barrier member, a first cuff and a second cuff. As discussed in more detail below, the methods may include attaching the discrete barrier member to the first cuff and the second cuff. The attachment of the discrete barrier member to the first and second cuffs may allow the barrier member to provide the desired tension across the absorbent article to maintain contact with the wearer during use and to maintain adequate separation of feces and urine in the absorbent article. Further to the above, the discrete barrier member may be attached to the topsheet of the absorbent article. The attachment of the barrier member to the topsheet may allow the discrete barrier member to remain in contact with the topsheet and, thus, to maintain the separation of the feces and urine once disposed on the absorbent article.

As discussed in more detail below, the methods according to the present disclosure may be utilized in the production of various components of absorbent articles, such as diapers. To help provide additional context to the subsequent discussion of the process embodiments, the following provides a general description of absorbent articles in the form of diapers that include components including the materials that may be used by the methods and apparatuses discussed herein.

Figure 4:
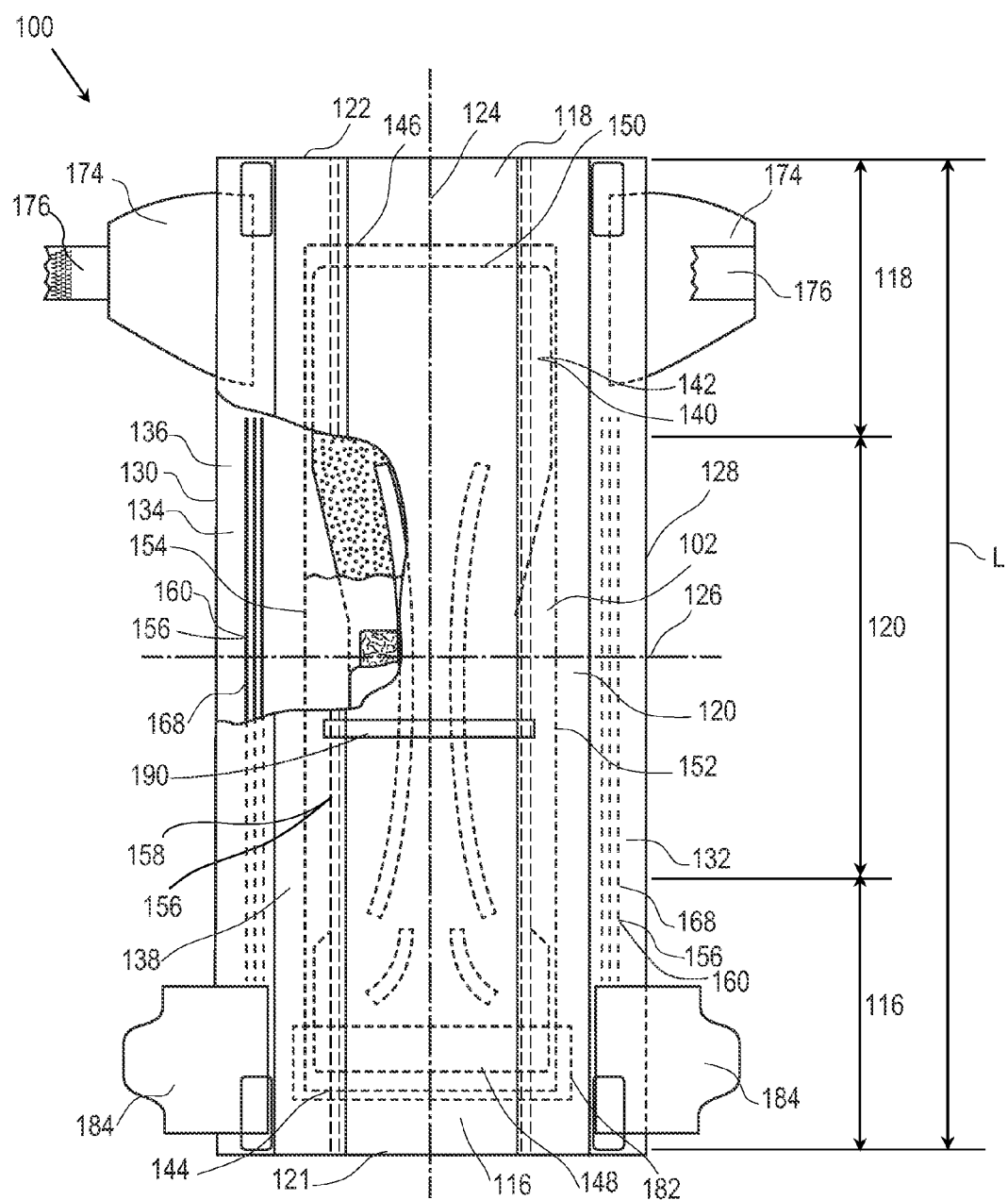
FIG. 4 is a partially cut away plan view of a diaper in accordance with one non-limiting embodiment of the present disclosure.

FIGS. 1, 2, and 4 illustrate an example of an absorbent article 100, such as a diaper, that may be assembled with the methods discussed herein. In particular, FIG. 1 shows a perspective view of an absorbent article 100 in a pre-fastened configuration, and FIG. 2 shows a plan view of the absorbent article 100 with the portion of the diaper that faces away from a wearer oriented towards the viewer. The absorbent article 100 shown in FIGS. 1 and 2 includes a chassis 102 and a ring-like elastic belt 104. As discussed below in more detail, a first elastic belt 106 and a second elastic belt 108 are connected together to form the ring-like elastic belt 104.

With continued reference to FIG. 2, the chassis 102 includes a first waist region 116, a second waist region 118, and a crotch region 120 disposed intermediate the first and second waist regions. The first waist region 116 may be configured as a front waist region, and the second waist region 118 may be configured as back waist region. In some embodiments, the length of each of the front waist region, back waist region, and crotch region 120 may be ⅓ of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the absorbent article 100 and chassis 102 of FIG. 2 is shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1, 2, and 4, the absorbent article 100 may include an inner, body facing surface 132, and an outer, garment facing surface 134. The chassis 102 may include a backsheet 136 and a topsheet 138. The chassis 102 may also include an absorbent assembly 140 including an absorbent core 142 that may be disposed between a portion of the topsheet 138 and the backsheet 136. As discussed in more detail below, the absorbent article 100 may also include other features, such as leg elastics and/or leg cuffs to enhance the fit around the legs of the wearer.

As shown in FIG. 2, the periphery of the chassis 102 may be defined by the first longitudinal side edge 128, a second longitudinal side edge 130; a first laterally extending end edge 144 disposed in the first waist region 116; and a second laterally extending end edge 146 disposed in the second waist region 118. Both side edges 128 and 130 extend longitudinally between the first end edge 144 and the second end edge 146. When the absorbent article 100 is worn on the lower torso of a wearer, the front waist edge 121 and the back waist edge 122 of the chassis 102 may encircle a portion of the waist of the wearer. At the same time, the chassis side edges 128 and 130 may encircle at least a portion of the legs of the wearer. Moreover, the crotch region 120 may be generally positioned between the legs of the wearer with the absorbent core 142 extending from the front waist region 116 through the crotch region 120 to the back waist region 118.

It is also to be appreciated that a portion or the whole of the absorbent article 100 may also be made laterally extensible. The additional extensibility may help allow the absorbent article 100 to conform to the body of a wearer during movement by the wearer. The additional extensibility may also help, for example, allow the diaper 100, including a chassis 102 having a particular size before extension, to extend in the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas, and undergarments. The backsheet 136 may also include a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also include an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the absorbent article 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets, and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

The absorbent article 100 may also include an absorbent assembly 140 that is joined to the chassis 102. As shown in FIGS. 2 and 4, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core may comprise a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

The absorbent article 100 may also include elasticized leg cuffs 156. It is to be appreciated that the leg cuffs 156 may be and are sometimes also referred to as leg bands, side flaps, barrier cuffs, elastic cuffs, or gasketing cuffs. The elasticized leg cuffs 156 may be configured in various ways to help reduce the leakage of body exudates in the leg regions. For example, in some embodiments, a gasketing leg cuff 160 may be positioned adjacent to the side edge 130, 128 of the chassis 102 and a barrier leg cuff 158 may be positioned between a gasketing leg cuff 160 and the longitudinal axis 124 of the absorbent article 100. Example leg cuffs 156 may include those described in U.S. Pat. Nos. 3,860,003; 4,909,803; 4,695,278; 4,795,454; 4,704,115; 4,909,803; U.S. Patent Publication No. 2009/0312730A1; and U.S. Patent Publication No. 2013/0255865A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, the absorbent article may have a continuous perimeter waist opening 110 and continuous perimeter leg openings 112 such as shown in FIG. 1. As previously mentioned, the ring-like elastic belt 104 is defined by a first elastic belt 106 connected with a second elastic belt 108. As shown in FIG. 2, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 118 of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 109a may also define the front waist edge 121 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts may include a nonwoven web of synthetic fibers, and may include a stretchable nonwoven. In other embodiments, the first and second elastic belts may include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 2, 3A, and 3B, the belt elastic material may include a plurality of elastic strands 168 that may be referred to herein as outer, waist elastics 170 and inner, waist elastics 172.

As shown in FIG. 2, the outer, waist elastics 170 extend continuously laterally between the first and second opposing end regions 106a, 106b and across the central region 106c of the first elastic belt 106 and between the first and second opposing end regions 108a, 108b and across the central region 108c of the second elastic belt 108. In some embodiments, some elastic strands 168 may be configured with discontinuities in areas. For example, as shown in FIG. 2, the inner, waist elastics 172 extend intermittently along the first and second elastic belts 106, 108. More particularly, the inner, waist elastics 172 extend along the first and second opposing end regions 106a, 106b and partially across the central region 106c of the first elastic belt 106. The inner, waist elastics 172 also extend along the first and second opposing end regions 108a, 108b and partially across the central region 108c of the second elastic belt 108. As such, the inner, waist elastics 172 do not extend across the entirety of the central regions 106c, 108c of the first and second elastic belts 106, 108. Thus, some elastic strands 168 may not extend continuously through regions of the first and second elastic belts 106, 108 where the first and second elastic belts 106, 108 overlap the absorbent assembly 140. In some embodiments, some elastic strands 168 may partially extend into regions of the first and second elastic belts 106, 108 where the first and second elastic belts 106, 108 overlap the absorbent assembly 140. In some embodiments, some elastic strands 168 may not extend into any region of the first and second elastic belts 106, 108 where the first and second elastic belts 106, 108 overlap the absorbent assembly 140. It is to be appreciated that the first and/or second elastic belts 106, 108 may be configured with various configurations of discontinuities in the outer, waist elastics 170 and/or the inner, waist elastic elastics 172.

In some embodiments, the elastic strands 168 may be disposed at a constant interval in the longitudinal direction. In other embodiments, the elastic strands 168 may be disposed at different intervals in the longitudinal direction. As discussed in more detail below, the belt elastic strands 168, in a stretched condition, may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2.

Referring to FIG. 4, in some embodiments, the absorbent article 100 may include a fastening system. The fastening system can be used to provide lateral tensions about the circumference of the absorbent article to hold the absorbent article on the wearer. The fastening system may comprise a fastener such as tape tabs, hook and loop fastening components, interlocking fasteners such as tabs and slots, buckles, buttons, snaps, and/or hermaphroditic fastening components. A landing zone 182 may be provided on the front waist region 116 for at least a portion of the fastener to be releasably attached to. Exemplary fastening systems may include those described in U.S. Pat. Nos. 3,848,594; 4,662,875; 4,846,815; 4,894,060; 4,946,527; 5,151,092; and 5,221,274.

As illustrated in FIG. 4, the absorbent article 100 may comprise front ears 184 and back ears 174. The front ears 184 and the back ears 174 may be an integral part of the chassis 102. For example, the front ears 184 and the back ears 174 may be formed from the topsheet 138 and/or the backsheet 136. Alternatively, the front ears 184 and the back ears 174 may be attached to the backsheet 136 and/or the topsheet 138. The front ears 184 and the back ears 174 may be extensible to facilitate attachment on the landing zone 182 and to maintain placement around the waist of the wearer. The back ears 174 may comprise a tab member 176. The tab member 176 may be attached to a portion of the back ears 174 to facilitate attachment to the landing zone 182.

The absorbent article 100 may also comprise a discrete barrier member 190, as illustrated in FIGS. 2 and 4. An exemplary discrete barrier member may include that described in U.S. Patent Application Nos. 61/918954; 61/919067; 61/918966; and 61/918978. The discrete barrier member 190 may be positioned in the crotch region 120 of the absorbent article 100. More specifically, the discrete barrier member 190 may be positioned a distance from the front edge 121 of the absorbent article 100. The distance may be 25% to 50% and/or 30% to 45% of the total length L of the absorbent article 100 taken from the front edge 121 to the rear edge 122 of the absorbent article 100. The discrete barrier member 190 may be positioned such that it extends substantially perpendicular to the longitudinal axis 124 of the absorbent article 100. Similarly, the discrete barrier member 190 may be positioned such that it extends substantially parallel to the lateral axis 126 of the absorbent article 100. The discrete barrier member 190 may be extensible in at least one of the longitudinal direction and the lateral direction.

As previously mentioned, the methods according to the present disclosure may be utilized to assemble discrete absorbent articles 100 and/or various components of absorbent articles 100, such as for example, chassis 102, elastic belts 106, 108, leg cuffs 156, and/or discrete barrier members 190. Although the following methods may be provided in the context of absorbent articles 100, as shown in FIGS. 1, 2, and 4, it is to be appreciated that the methods and apparatuses herein may be used with various process configurations and/or absorbent articles, such as for example, disclosed in U.S. Pat. No. 7,569,039; U.S. Patent Publication Nos. 2005/0107764A1, 2012/0061016A1, and 2012/0061015A1; 2013/0255861A1; 2013/0255862A1; 2013/0255863A1; 2013/0255864A1; and 2013/0255865A1, all of which are incorporated by reference herein.

Figure 5A:
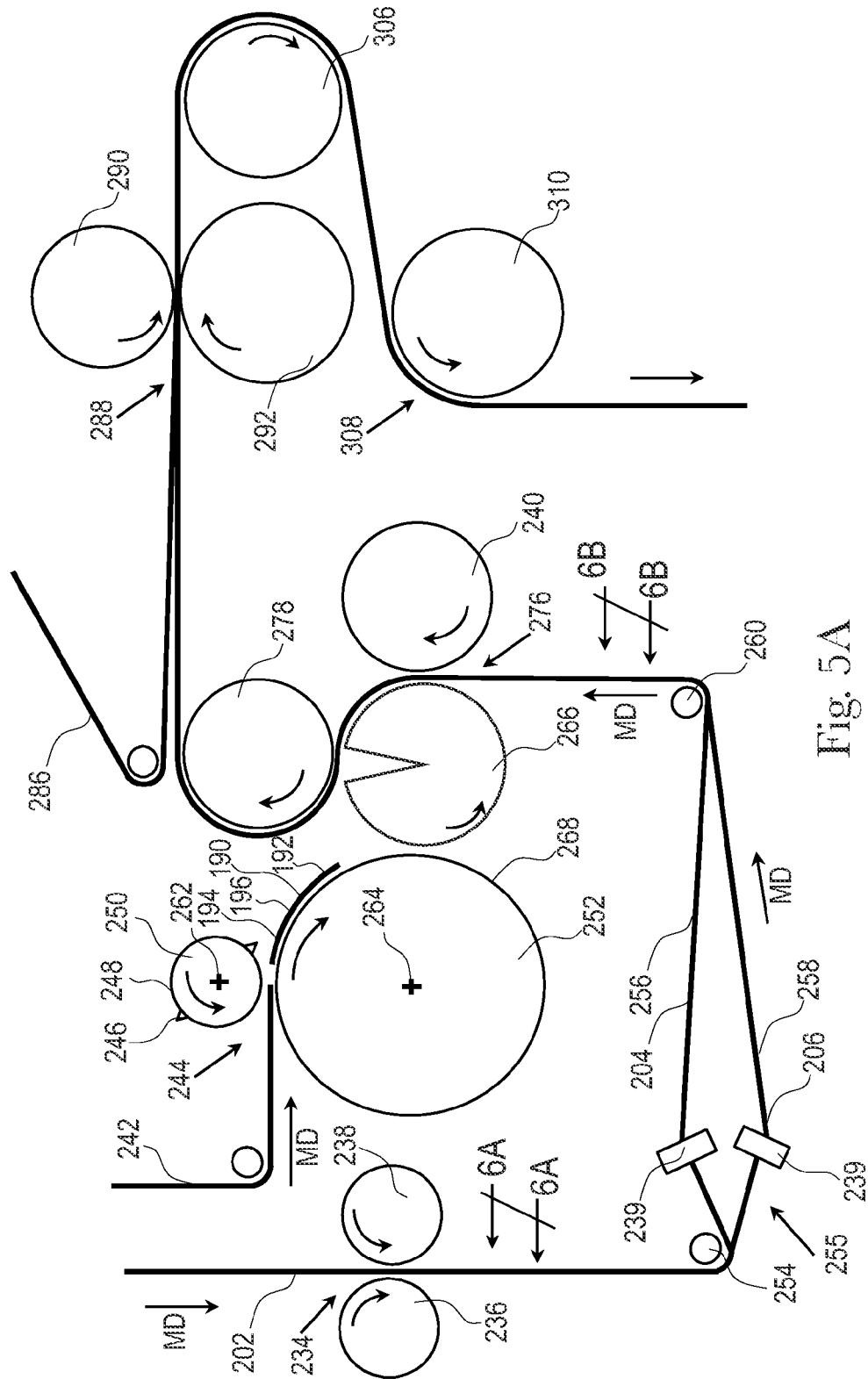
FIG. 5A is a schematic representation of a process used to manufacture absorbent articles comprising a discrete barrier member in accordance with one non-limiting embodiment of the present disclosure.

FIG. 5A shows an exemplary schematic representation of a method that may be used to manufacture an absorbent article 100, as previously described, including a discrete barrier member 190. Generally, the method may include advancing a cuff substrate 202 in a machine direction MD. The cuff substrate 202 may be used to form leg cuffs 156, for example, as shown in FIGS. 2 and 4. The cuff substrate 202 may be slit into a first cuff substrate 204 and a second cuff substrate 206. The first cuff substrate 204 and the second cuff substrate 206 may be advanced to a repositioning device 255. The repositioning device 255 may separate the first cuff substrate 204 from the second cuff substrate 206 at a desired distance in the cross direction, referred to herein as a first distance. Once the first cuff substrate 204 and the second cuff substrate 206 have been repositioned, the first and second cuff substrates 204, 206 may be advanced to a first bonding area 276.

In addition, a barrier substrate 244 may be advanced in the machine direction MD to a cutting device 244. The cutting device 244 may cut the barrier substrate 244 to form a discrete barrier member 190. The discrete barrier member 190 may be folded, at a folding roll 266, and advanced to the first bonding area 276. At the first bonding area 276, the discrete barrier member 190 may be disposed on the first cuff substrate 204 and the second cuff substrate 206. In the first bonding area 276, a portion of the discrete barrier member 190 may be connected to at least a portion of the first cuff substrate 204 and the second cuff substrate 206. Upon exiting the first bonding area 276, the discrete barrier member 190, first cuff substrate 204, and second cuff substrate 206 may be advanced to accept a topsheet substrate 286. The topsheet substrate 286 may be disposed on at least a portion of the discrete barrier member 190, the first cuff substrate 204, and the second cuff substrate 206. Once the topsheet substrate 286 has been disposed on the discrete barrier member 190 and the first and second cuff substrates 204, 206, these substrates may be advanced through a second bond area 288 and a third bond area 308. The second and third boding areas 288, 308, may bond any one of the topsheet substrate 286, the first cuff substrate 204, the second cuff substrate 206, and the discrete barrier member 190. This process will be described in more detail herein.

As previously described, the cuff substrate 202 may be separated by a slitting device 234, as shown in FIG. 5A. The slitting device 234 may include a slitting roll 236 including one or more blades extending radially outward and an anvil roll 238 including an anvil. Other slitting devices may be used such as those available from Tidland Products, Camas, Wash. The slitting device 234 may separate the cuff substrate 202 into a first cuff substrate 204 and a second cuff substrate 206, as illustrated in FIG. 6A.

Figure 6A:
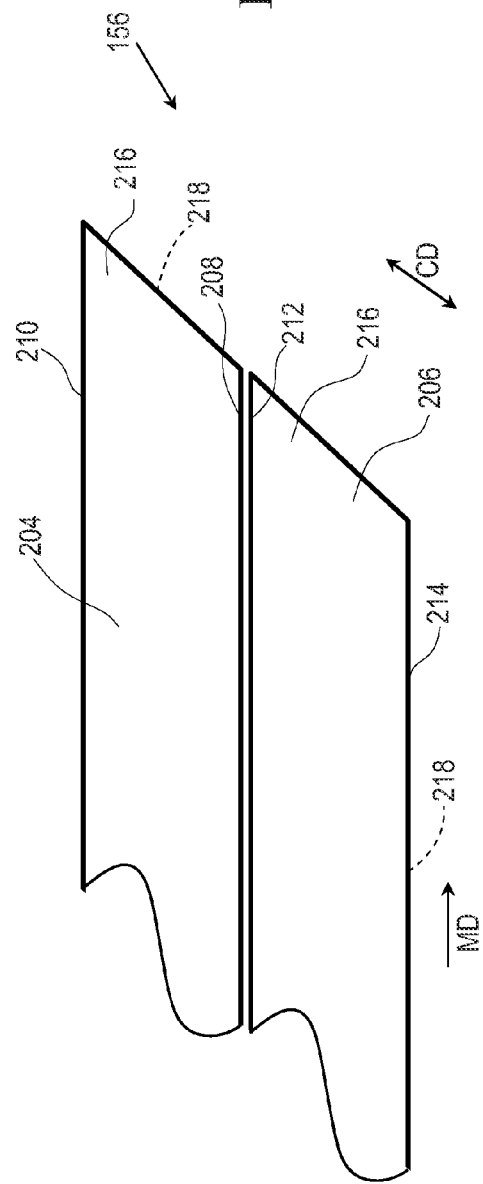
FIG. 6A is a perspective view of a first cuff substrate and a second cuff substrate of FIG. 5A taken along line 6A-6A in accordance with one non-limiting embodiment of the present disclosure.

Still referring to FIG. 6A, the first cuff substrate 204 may include a first inner cuff edge 208 and a first outer cuff edge 210, opposite to the first inner cuff edge 208. The second cuff substrate 206 may include a second inner cuff edge 212 and a second outer cuff edge 214, opposite the second inner cuff edge 212. The first and second inner cuff edges 208, 212 and the first and second outer cuff edges 210, 214 extend in a direction substantially parallel to the machine direction MD. Further, the first cuff substrate 204 and the second cuff substrate 206 may include a first cuff surface 216 and a second cuff surface 218. It is to be appreciated that one or more elastics may be disposed on each cuff substrate to form a leg cuff 156, as previously discussed. Further, it is also to be appreciated that an additional substrate may be disposed on the one or more elastics. However, FIG. 6A is a simplified schematic representation.

Figure 6B:
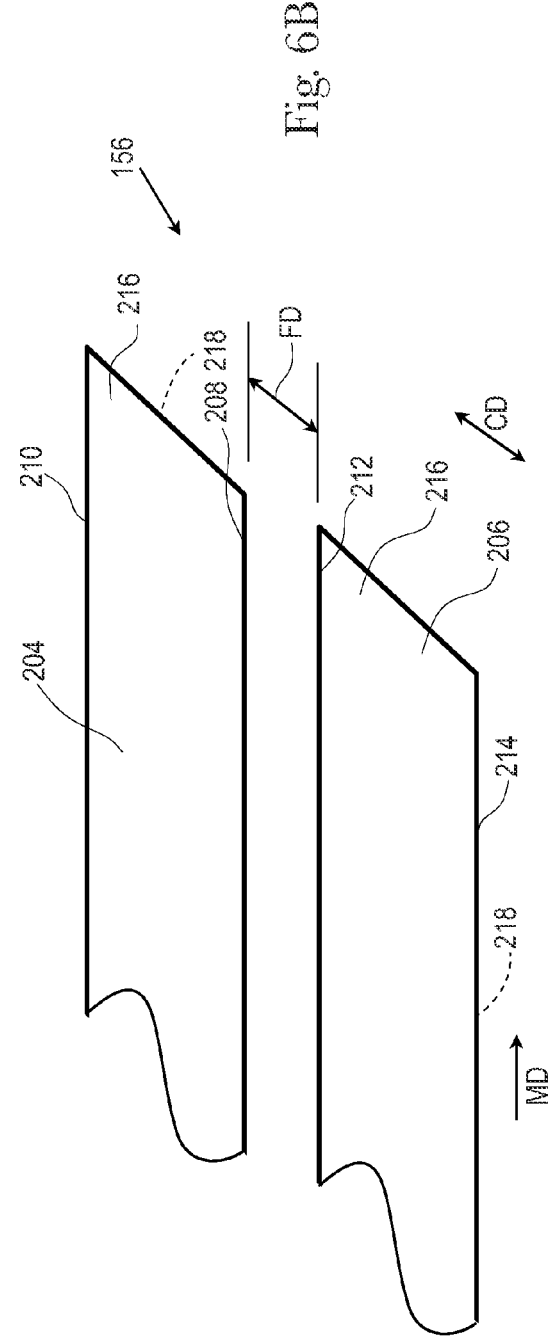
FIG. 6B is a perspective view of a first cuff substrate and a second cuff substrate of FIG. 5A taken along line 6B-6B in accordance with one non-limiting embodiment of the present disclosure.

Referring to FIG. 5A, it is to be appreciated that the first inner cuff edge 208 may not be the desired distance from the second inner cuff edge 212 after the cuff substrate 202 was slit. Stated another way, the first cuff substrate 204 and the second cuff substrate may not be appropriately spaced for additional materials to be added to the first and second cuff substrates in subsequent processes. Thus, to adjust the spacing between the first inner cuff edge 208 and the second inner cuff edge 212, each of the first cuff substrate 204 and the second cuff substrate 206 may be directed to a separating device 255. The separating device 255, as shown in FIG. 5A, may reposition the first cuff substrate 204 and the second cuff substrate 206. More specifically, the first cuff substrate 204 and the second cuff substrate 206 may be advanced toward and, subsequently, diverge at a first roll 254. Each of the first cuff substrate 204 and the second cuff substrate 206 may pass through a canted idler 239, which allows the cuff substrates to diverge in the cross direction CD. Upon diverging, the first cuff substrate 204 may advance down a first lane 256 and the second cuff substrate 206 may advance down a second lane 258. Subsequently, the first cuff substrate 204 and the second cuff substrate 206 may be directed to converge at a second roll 260. The first cuff substrate 204 and the second cuff substrate 206 may be placed about the second roll 260 such that the first inner cuff edge 208 and the second inner cuff edge 212 may be separated by a first distance FD, as illustrated in FIG. 6B. The first distance FD may be from about 5 mm to about 100 mm and/or about 10 mm to about 85 mm and/or about 15 mm to about 65 mm and/or about 20 mm to about 45 mm, including all 0.5 mm increments therebetween. Once the first cuff substrate 204 and the second cuff substrate are placed in the desired position, the first cuff substrate 204 and the second cuff substrate 206 may be directed to a first bonding area 276.

Figure 5B:
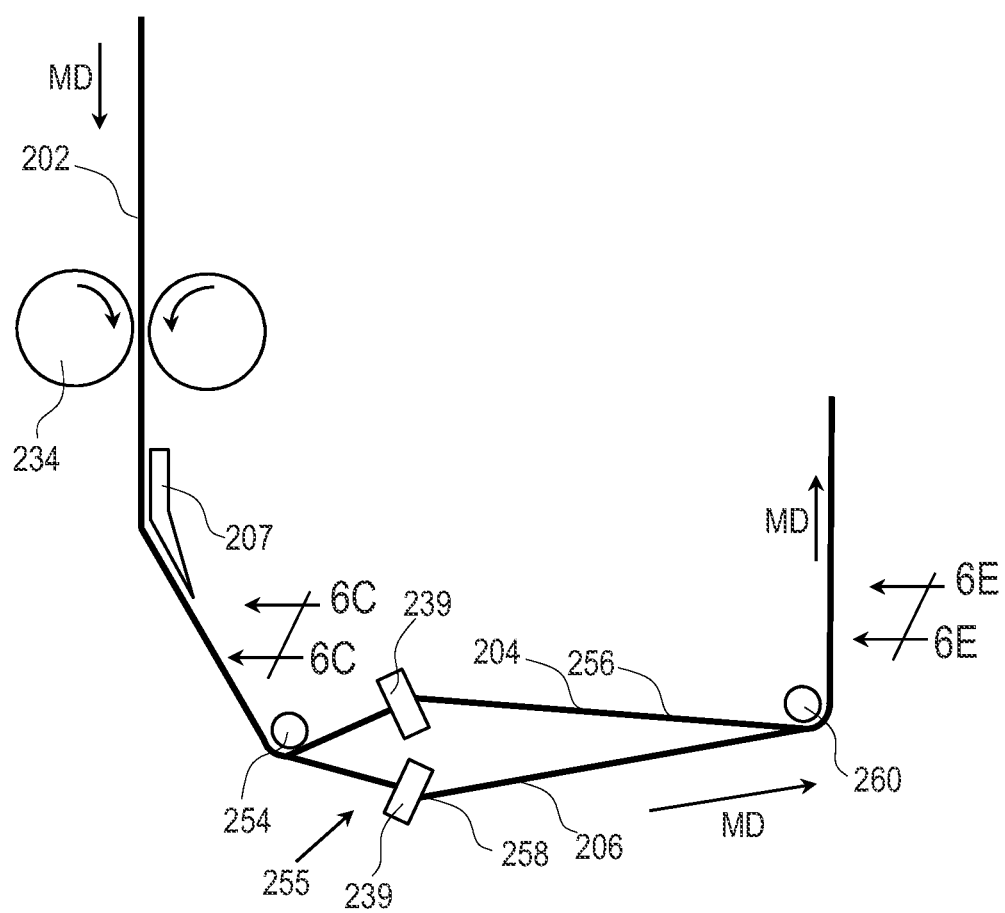
FIG. 5B is a schematic representation of a portion of the process used to manufacture absorbent articles comprising a discrete barrier member in accordance with one non-limiting embodiment of the present disclosure.

In some embodiments, after slitting the cuff substrate 202, the first cuff substrate 204 and the second cuff substrate 206 may be advanced in the machine direction MD through a folding device 207, as illustrated in FIG. 5B. The folding device 207 may be adapted to fold the first cuff substrate 204 and the second cuff substrate 206, as illustrated, for example, in FIGS. 6C and 6D. In some exemplary embodiments, the first cuff substrate 204 and the second cuff substrate 206 may be folded to substantially surround one or more elastics disposed on the cuff substrate (not shown). The first cuff substrate 204 and the second cuff substrate 206 may include a first cuff surface 216 and a second cuff surface 218. The first cuff surface 216 and the second cuff surface 218 may each include an inner edge region 220, an outer edge region 222 opposite the inner edge region 220, and a central region 224 between the inner edge region 220 and the outer edge region 222. The first cuff substrate 204 may be folded such that the first inner cuff edge 208 is associated with the inner edge region 220 of the first cuff substrate 204, as shown in FIG. 6C. The folded first cuff substrate 204 may form a first cuff fold 226 that includes a first fold edge 228. Likewise, the second cuff substrate 206 may be folded such that the second inner cuff edge 212 is associated with the inner edge region 220 of the second cuff substrate 206, as shown in FIG. 6C. The folded second cuff substrate 206 may form a second cuff fold 230 that includes a second fold edge 232. The first cuff substrate 204 and the second cuff substrate 206 may be positioned such that the first fold edge 228 is an initial distance ID away from the second fold edge 232. In some embodiments, the initial distance ID may be from about 5 mm to about 45 mm and/or about 10 mm to about 35 mm and/or about 15 mm to about 25 mm, including all 0.5 mm increments therebetween. It is to be appreciated that the first cuff substrate 204 and the second cuff substrate may be folded in various ways and may include additional components, such as for example, in accordance with the methods and apparatuses disclosed in U.S. Patent Publication Nos. 2013/0255861A1; 2013/0255862A1; 2013/0255863A1; 2013/0255864A1; and 2013/0255865A1.

FIG. 6D illustrates an exemplary embodiment of a folded first cuff substrate 204 and a second cuff substrate 206. The first cuff substrate 204 may be folded such that the first inner cuff edge 208 is associated with at least a portion of the central region 224 of the first cuff substrate 204. The folded first cuff substrate 204 may form a first cuff fold 226 that includes a first fold edge 228. Likewise, the second cuff substrate 206 may be folded such that the second inner cuff edge 212 is associated with at least a portion of the central region 224 of the second cuff substrate 206, as shown in FIG. 6D. The folded second cuff substrate 206 may form a second cuff fold 230 that includes a second fold edge 232. The first cuff substrate 204 and the second cuff substrate 206 may be positioned such that the first fold edge 228 is an initial distance away from the second fold edge 232. The initial distance ID may be from about 5 mm to about 45 mm and/or about 10 mm to about 35 mm and/or about 15 mm to about 25 mm, including all 0.5 mm increments therebetween.

It is to be appreciated that first cuff substrate 204 and the second cuff substrate 206 may be folded such that the first inner cuff edge 208 is associated with any one of the outer edge region 222, the central region 224, and the inner edge region. Further, the first cuff substrate 204 and the second cuff substrate may be folded such that each of the first inner cuff edge 208 and the second inner cuff 212 edge do not associate with the same region of the cuff surface. For example, the first cuff substrate 204 may be folded such that the first inner cuff edge 208 is associated with the outer edge region 222, and the second cuff substrate 204 may be folded such that the second inner cuff edge 212 is associated with the central region 224.

Figure 6E:
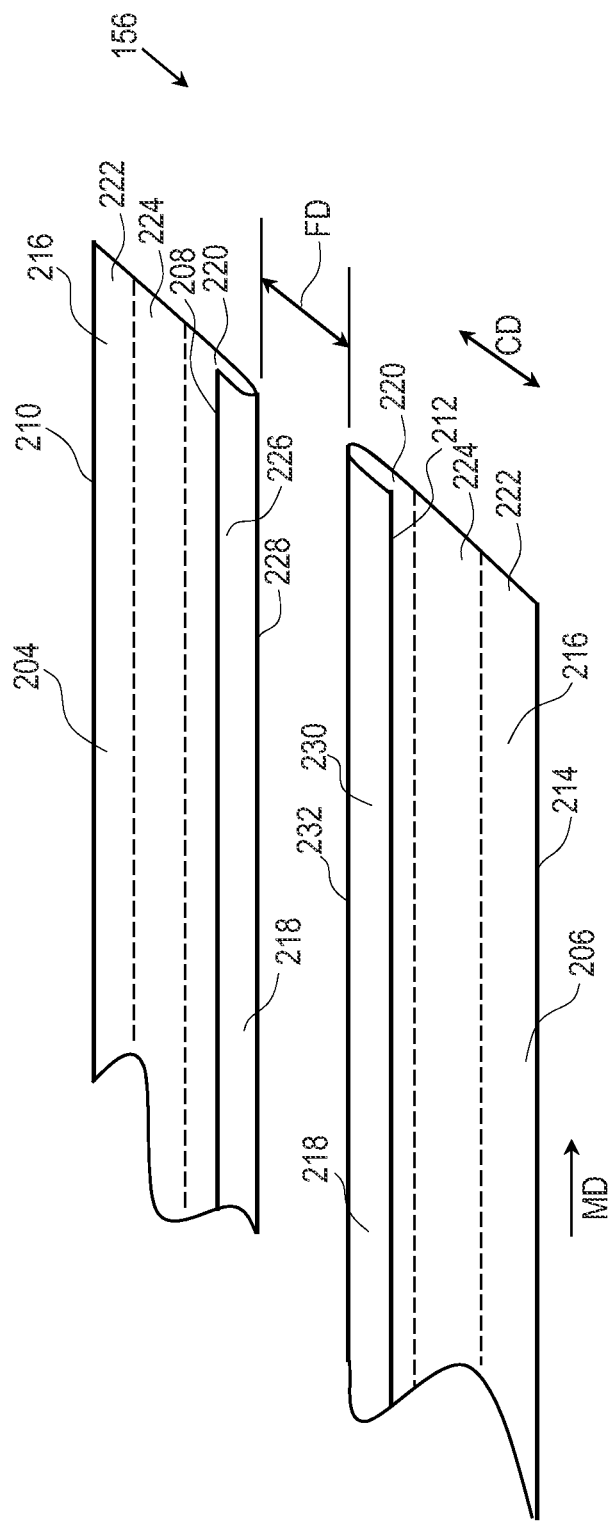
FIG. 6E is a perspective view of a first cuff substrate and a second cuff substrate of FIG. 5B taken along line 6E-6E in accordance with one non-limiting embodiment of the present disclosure.

Referring to FIGS. 5B and 6E, it is to be appreciated that the first fold edge 228 may not be the desired distance from the second fold edge 230 after each of the first cuff substrate 206 and the second cuff substrate 208 are separated and/or folded. Stated another way, the initial distance ID may not be the appropriate spacing between the first cuff substrate 204 and the second cuff substrate 206 for additional materials to be added to the first and second cuff substrates in subsequent processes. Thus, to adjust the spacing between the first fold edge 228 and the second fold edge 230, each of the first cuff substrate 204 and the second cuff substrate 206 may be directed to a separating device 255. The separating device 255 may include a first roll 254, a canted idler 239, a first lane 256, a second lane 258, and a second roll 260. More specifically, the first cuff substrate 204 and the second cuff substrate 206 may be advanced toward and, subsequently, diverge at a first roll 254 and pass over the canted idler 239. Upon diverging, the first cuff substrate 204 may advance down a first lane 256 and the second cuff substrate 206 may advance down a second lane 258. Subsequently, the first cuff substrate 204 and the second cuff substrate 206 may be directed to converge at a second roll 260. The first cuff substrate 204 and the second cuff substrate 206 may be placed about the second roll 260 such that the first fold edge 228 may be a first distance FD from the second fold edge 230, as illustrated in FIG. 6E. The first distance FD may be from about 5 mm to about 100 mm and/or about 10 mm to about 85 mm and/or about 15 mm to about 65 mm and/or about 20 mm to about 40 mm, including all 0.5 mm increments therebetween. Once the first cuff substrate 204 and the second cuff substrate are placed in the desired position, the first cuff substrate 204 and the second cuff substrate 206 may be directed to a first bonding area 276.

Figure 5C:
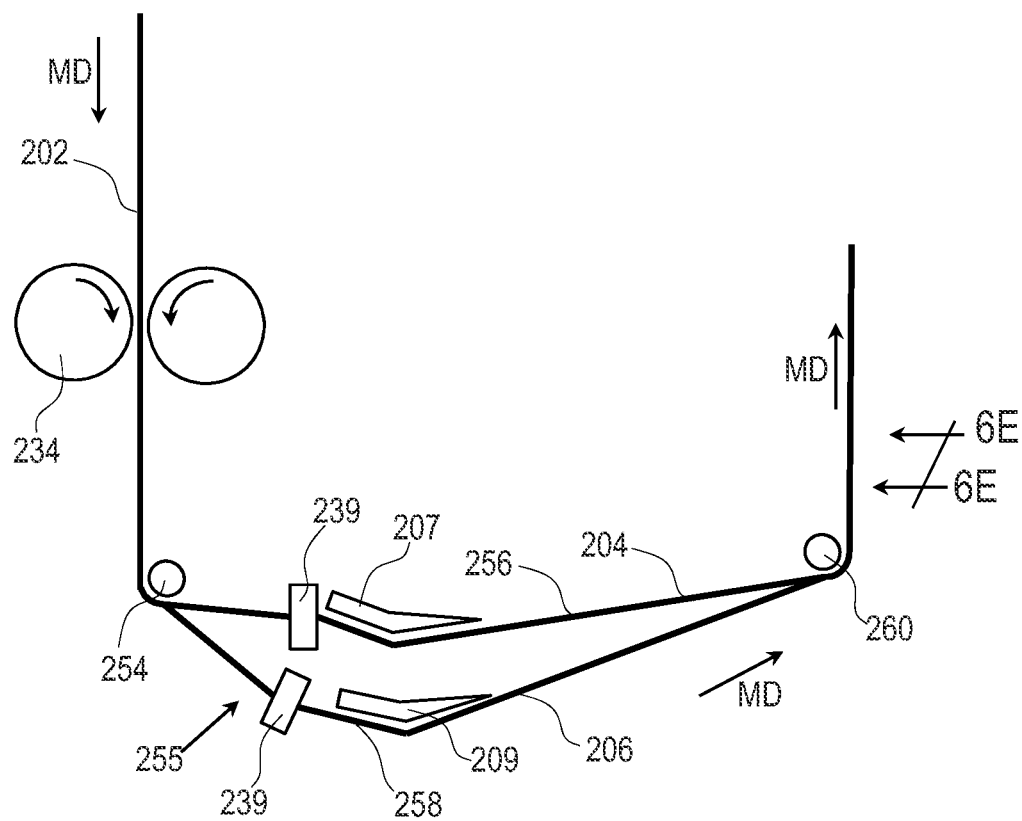
FIG. 5C is a schematic representation of a portion of the process used to manufacture absorbent articles comprising a discrete barrier member in accordance with one non-limiting embodiment of the present disclosure.

Referring to FIGS. 5C and 6E, it is to be appreciated that the first fold edge 228 may not be the desired distance from the second fold edge 230 after each of the first cuff substrate 206 and the second cuff substrate 208 are separated. Stated another way, the initial distance ID may not be the appropriate spacing between the first cuff substrate 204 and the second cuff substrate 206 for additional materials to be added to the first and second cuff substrates in subsequent processes. Thus, to adjust the spacing between the first fold edge 228 and the second fold edge 230, each of the first cuff substrate 204 and the second cuff substrate 206 may be directed to a separating device 255. The separating device 255 may include a first roll 254, a canted idler 239, a first lane 256, a second lane 258, and a second roll 260. More specifically, the first cuff substrate 204 and the second cuff substrate 206 may be advanced toward and, subsequently, diverge at a first roll 254 and pass over the canted idler 239. Upon diverging, the first cuff substrate 204 may advance down a first lane 256 and the second cuff substrate 206 may advance down a second lane 258. Subsequently, the first cuff substrate 204 and the second cuff substrate 206 may be directed toward a folding device. The folding device may be a single device (not shown) that folds both of the first and second cuff substrate 204, 206 or multiple devices, as shown in FIG. 5C. As illustrated in FIG. 5C, the first cuff substrate 204 may be folded by a first folding device 207 and the second cuff substrate 206 may be folded by the second folding device 209. After being folded, the first cuff substrate 204 and the second cuff substrate 206 may be directed to converge at a second roll 260. The first cuff substrate 204 and the second cuff substrate 206 may be placed about the second roll 260 such that the first fold edge 228 may be a first distance FD from the second fold edge 230, as illustrated in FIG. 6E. The first distance FD may be from about 5 mm to about 100 mm and/or about 10 mm to about 85 mm and/or about 15 mm to about 65 mm and/or about 20 mm to about 40 mm, including all 0.5 mm increments therebetween. Once the first cuff substrate 204 and the second cuff substrate are placed in the desired position, the first cuff substrate 204 and the second cuff substrate 206 may be directed to a first bonding area 276.

It is to be appreciated that the first cuff substrate 204 and the second cuff substrate 206 may be positioned such that the first fold edge 228 is a desired distance from the second fold edge 232 after being slit and/or folded, and thus, repositioning the first cuff substrate 204 and the second cuff substrate 206 may be unnecessary. For example, the initial distance ID separating the first cuff substrate 204 and the second cuff substrate 206 may be equal to the first distance FD, or the desired distance for subsequent processes, and thus, need not undergo repositioning. In this instance, the first cuff substrate 204 and the second cuff substrate 206 may advance in the machine direction MD from at least one of the slitting device 236 and the folding device 207 to a first bonding area 276.

It is also to be appreciated that the first cuff substrate 204 and the second cuff substrate 206 need not be folded. The first cuff substrate 204 and the second cuff substrate 206 may proceed through the process unfolded, as shown in FIGS. 6A and 6B. However, the first cuff fold 226 and the second cuff fold 226 may provide additional strength for bonding, which will be described in more detail below. However, to be concise, the following illustrations and description will include that first cuff substrate 204 and second cuff substrate 206 are folded.

Figure 7:
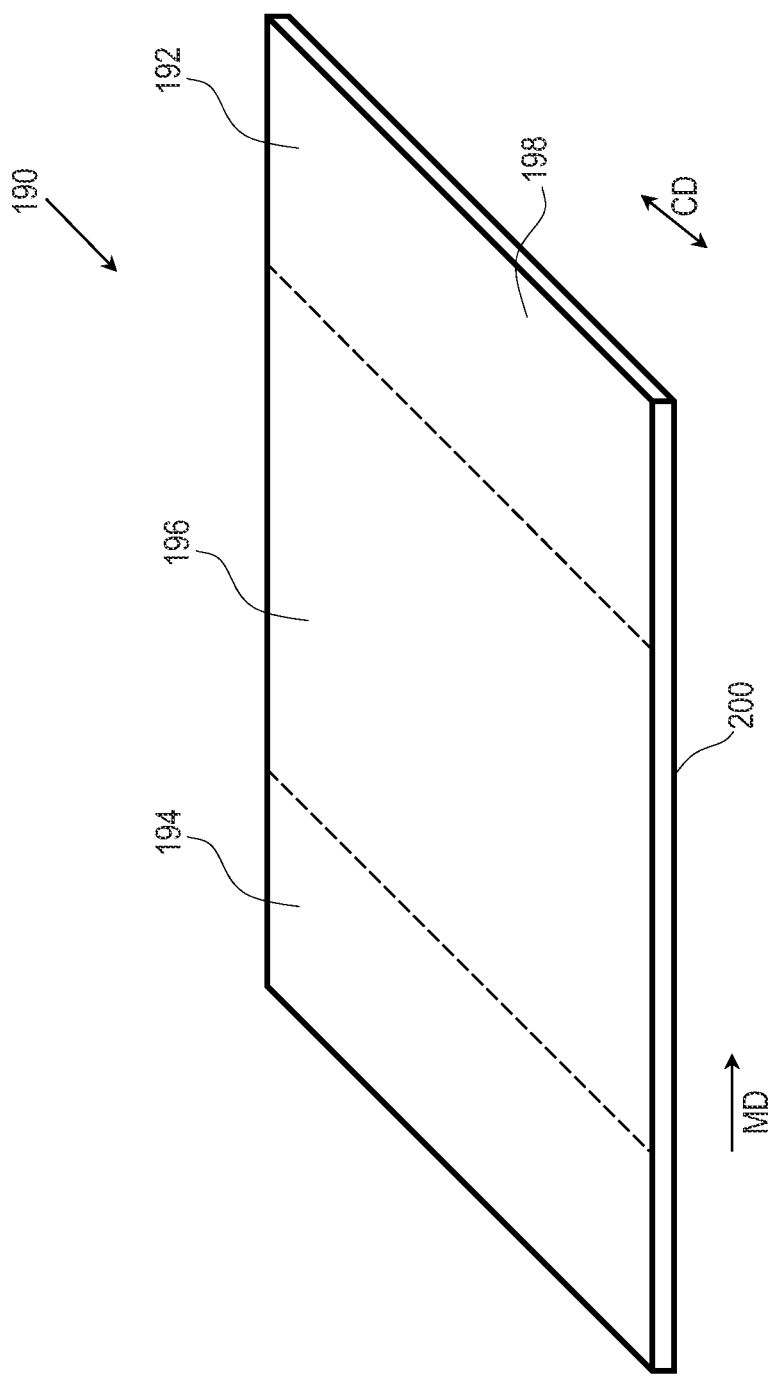
FIG. 7 is a perspective view of a discrete barrier member in accordance with one non-limiting embodiment of the present disclosure.

Referring to FIG. 5A, a barrier substrate 242 may be advanced toward a cut and slip device 244. The cut and slip device 244 may be used to space each discrete barrier member 190 from each other discrete barrier member 190. Example operations/equipment for achieving the spacing between the barrier members are disclosed in U.S. Pat. No. 5,702,551, sometimes referred to as a cut and slip operation/device. Other types of operations and equipment that may be used to cut and space discrete components are disclosed in U.S. Pat. Nos. 6,450,321; 6,705,453; and EP 0 812 789 A2. In some example embodiments, the cut and slip device 244 may include a cutting roll 250 that operatively engages a slip roll 252. The cutting roll 250 may include a blade 246 that extends radially outward from the surface 248 of the cutting roll 250. The cutting roll 250 may rotate about a central axis 262 causing the blades 246 to rotate about the central axis 262. The blade 246 may engage the barrier substrate 242 separating a portion of the barrier substrate 242 to form a discrete barrier member 190. The discrete barrier member 190 may include a leading edge portion 192, a trailing edge portion 194 opposite the leading edge portion, and a central portion 196 between the leading edge portion 192 and the trailing edge portion 194, as shown in FIGS. 5A and 7. The discrete barrier member 190 may also include a first surface 198 and a second surface 200 opposite the first surface 198. The discrete barrier member 190 may be extensible in at least one of the machine direction and the cross direction.

The slip roll 252 may rotate about a central axis 264 to advance the discrete barrier member 190 toward a folding roll 266, as shown in FIG. 5A. More specifically, the second surface 200 of the discrete barrier member 190 may be in facing relationship with the outer surface 268 of the slip roll 252. The discrete barrier member 190 may advance in the machine direction MD about the central axis 264 of the slip roll 252 such that the leading edge portion 192 may be the first to associate with the folding roll 266.

Figure 8:
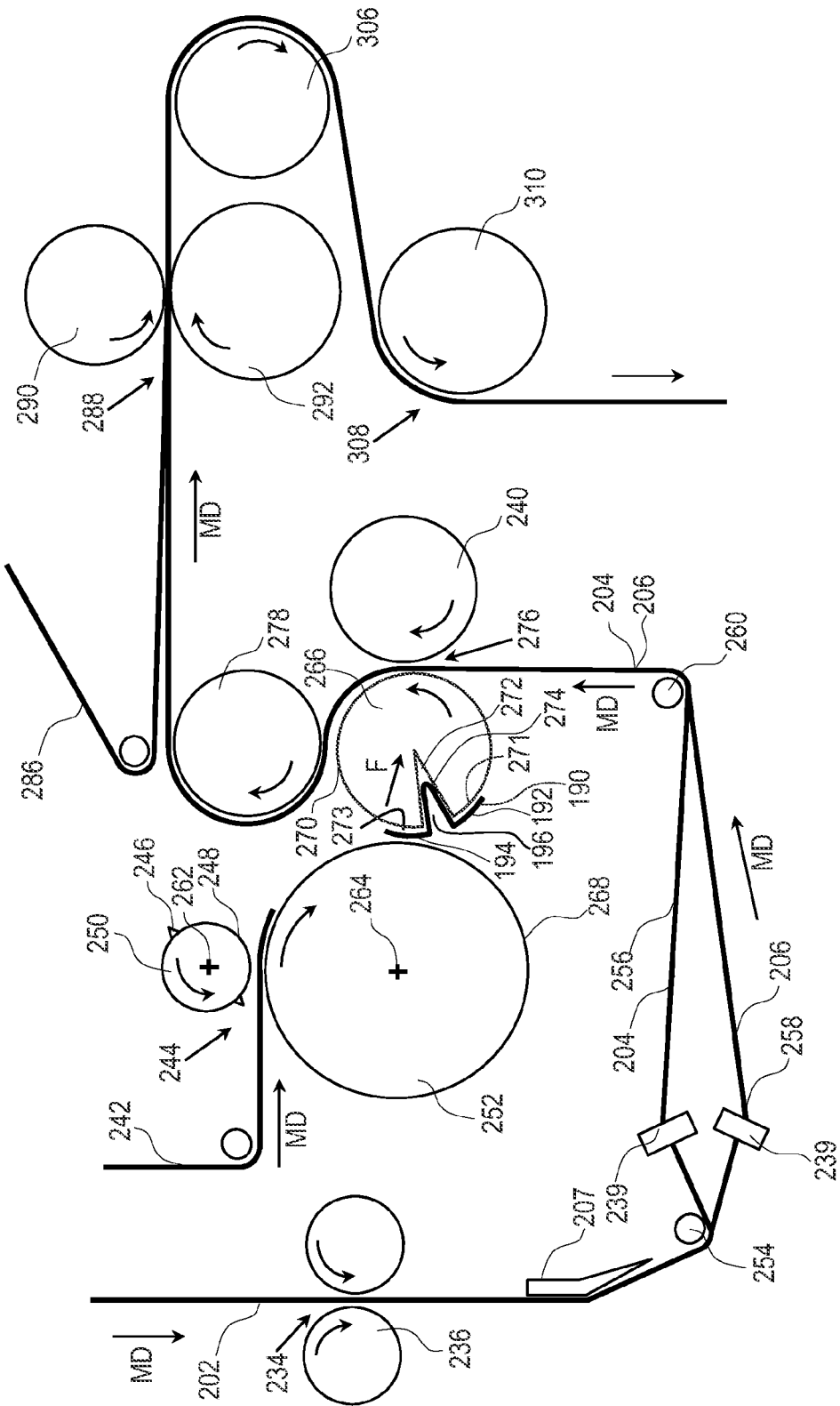
FIG. 8 is a schematic representation of a process used to manufacture absorbent articles comprising a discrete barrier member in accordance with one non-limiting embodiment of the present disclosure.

Upon disassociating with the slip roll 252 the discrete barrier member 190 may be folded. As illustrated in FIG. 8, the discrete barrier member 190 may be transferred from the slip roll 252 to the folding roll 266, such as disclosed for example in U.S. Patent Application No. 62/004,240. The folding roll 266 may include an outer surface 270 that includes a first engagement portion 271, a second engagement portion 273 opposite the first engagement portion, and a groove portion 272. Further, the folding roll 266 may be in fluid communication with a vacuum source (not shown) such that a vacuum force F may act on at least a portion of the discrete barrier member 190. The vacuum force F may act on the discrete barrier member 190 such that the first surface 198 associates with the outer surface 270 of the folding roll 266 and the discrete barrier member 190 remains associated with the folding roll 266 during rotation. The leading edge portion 192 may associate with the first engagement portion 271 of the folding roll 266. Similarly, the trailing edge portion 194 may associate with the second engagement portion 273 of the folding roll 266. The central portion 196 of the discrete barrier member 190 may associate with the groove portion 272. The vacuum force F may cause the central portion 196 of the discrete barrier member 190 to associate with the groove portion 272 forming a fold 274 in the discrete barrier member 190. It is to be appreciated that the groove portion 272 may include any number of topographies that may be used to fold the discrete barrier member. The discrete barrier member 190 may be advanced toward the first bond roll 240, the first cuff substrate 204, and the second cuff substrate 206.

The leading edge portion 192 of the discrete barrier member 190 may first associate with the first cuff substrate 204 and the second cuff substrate 206 as the folding roll 266 rotates. The discrete barrier member 190 associated with the first cuff substrate 204 and the second cuff substrate 206 may advance into a first bonding area 276. The first bonding area 276 may include the first bond roll 240. The first bond roll 240 may interact with the folding roll 266 to form a bond. In some embodiments, the first bond roll 240 may be an anvil roll including one or more bond patterns. In the first bonding area 276, at least a portion of the trailing edge portion 194 of the discrete barrier member 190 may be connected to the first cuff substrate 204 and the second cuff substrate 206. In some embodiments, the trailing edge portion 194 of the discrete barrier member 190 may be bonded to at least a portion of the first cuff fold 226 of the first cuff substrate 204 and to the second cuff fold 230 of the second cuff substrate 206.

Figure 10A:
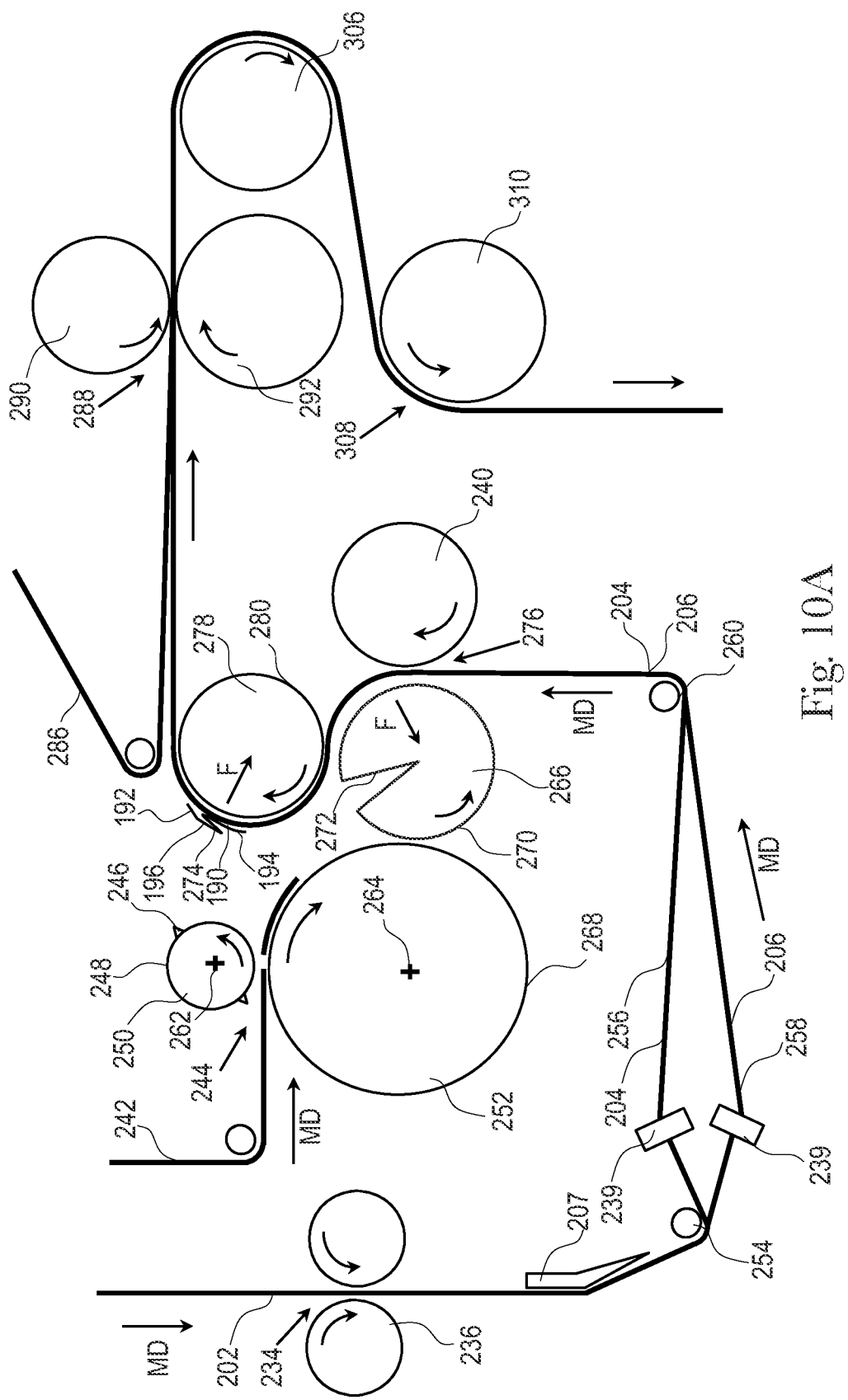
FIG. 10A is a schematic representation of a process used to manufacture absorbent articles comprising a discrete barrier member in accordance with one non-limiting embodiment of the present disclosure.
Figure 10B:
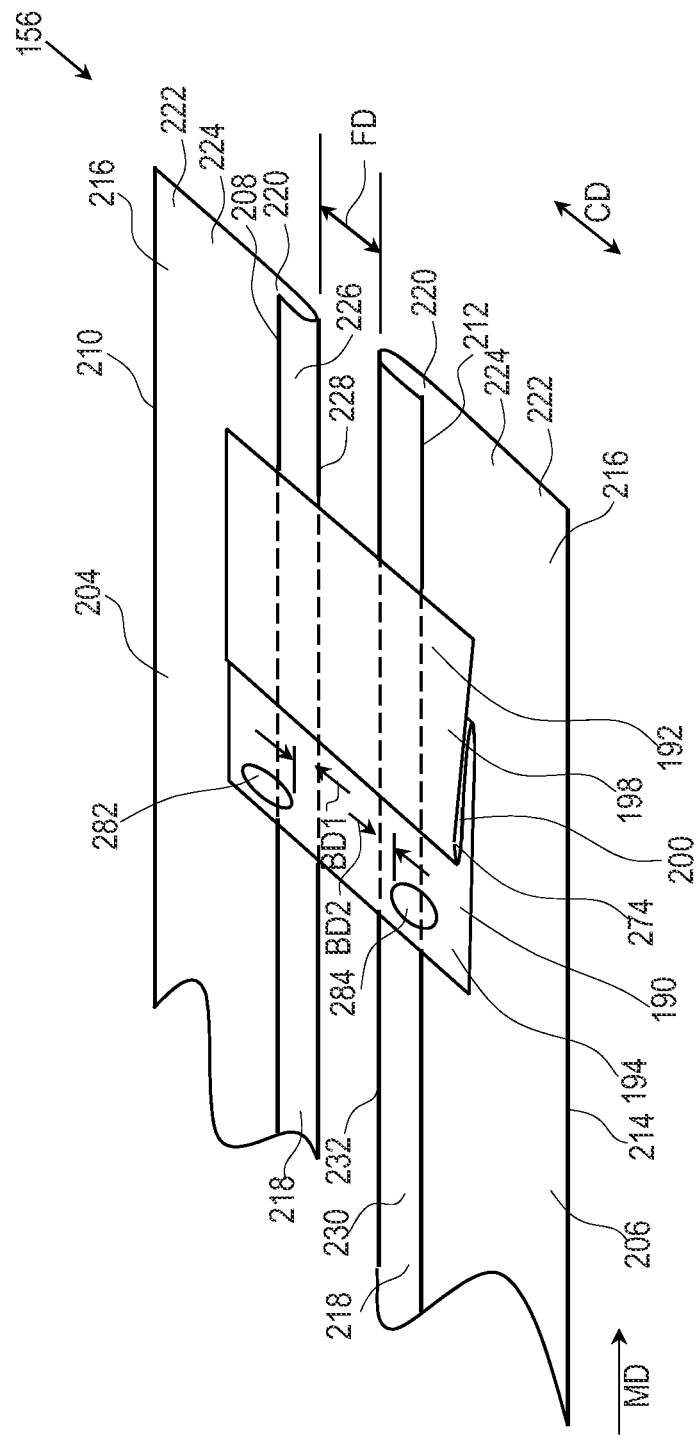
FIG. 10B is a perspective view of a discrete barrier member disposed on a first cuff substrate and a second cuff substrate in accordance with one non-limiting embodiment of the present disclosure.

The portion of the trailing edge portion 194 of the discrete barrier member 190 may be bonded at a first bond site 282 and a second bond site 284, as illustrated in FIG. 10B. The bond between the discrete barrier member 190 and the first and second cuff substrate 204, 206 may be by, for example, high pressure welding, hot air welding, heat crimping, or ultrasonic welding. Exemplary bonding methods and apparatuses may include those described in U.S. Pat. Nos. 4,854,984; 4,919,738; 5,711,847; 5,817,199; 6,123,792; 7,449,084; 6,248,195; 6,546,987; and U.S. patent application Ser. Nos. 14/038,812; 61/836,690; and 61/836,745. It is to be appreciated that the bond between the discrete barrier member 190 and the first and second cuff substrates 204, 206 may also include the use of adhesives alone or in addition to the aforementioned types of bonding. However, it has been found that limiting the use of adhesives in absorbent articles, such as diapers, is desirable to consumers and manufacturers. For consumers, the desire for limited use or non-use of adhesives may be a result of, for example, actual or perceived irritation of the wearer's skin. For manufacturers, the desire for limited use of adhesive may be a result of numerous challenges in handling the adhesive during the manufacturing process. For example, adhesive often require a certain period of time to adhere and/or solidify, which may cause a delay in the manufacturing process. Although adhesives may be used in absorbent articles, the absorbent article including a discrete barrier member of the present disclosure may be assembled without the use of adhesives. The bond formed at the first bond site 282 and the second bond site 284 may be strong enough to withstand a greater than 105% and/or greater than 125% and/or greater than 200% and/or greater than 250% elongation in the width of the discrete barrier member 190.

Further, the first bond site 282 may be positioned at a first bond distance BD1 from the first fold edge 228. The first bond distance BD1 is the substantially perpendicular distance from the first fold edge 228 to the first bond site 282. For example, the first bond distance BD1 may be from about 1 mm to about 20 mm and/or from about 2 mm to about 10 mm and/or from about 3 mm to about 5 mm, including all 0.5 mm increments therebetween. Likewise, the second bond site 284 may be posited a second bond distance BD2 from the second fold edge 232. The second bond distance BD2 is the substantially perpendicular distance form the second fold edge 232 to the second bond site 284. For example, the second bond distance BD2 may be from about 1 mm to about 20 mm and/or from about 2 mm to about 10 mm and/or from about 3 mm to about 5 mm, including all 0.5 mm increments therebetween. The second bond distance BD2 may be greater than, less than, or equal to the first bond distance BD1 It is to be appreciated that the bond distance may be measured from the first inner cuff edge 208 and the second inner cuff edge 212 if the first cuff substrate 204 and the second cuff substrate 206 are not folded.

The trailing edge portion 194 may associate with the first cuff substrate 204 and the second cuff substrate 206, as illustrated in FIG. 9. The discrete barrier member 190, the first cuff substrate 204, and the second cuff substrate may be advanced toward a vacuum roll 278. The vacuum roll 278 may be in fluid communication with a vacuum source (not shown). The vacuum source provides a vacuum force F on the discrete barrier member 190, the first cuff substrate 204, and the second cuff substrate 206 such that each maintains association with the outer surface 208 of the vacuum roll 278, as illustrated in FIG. 10A. More specifically, the second surface 200 of the discrete barrier member 190 may be associated with the first cuff substrate 204 and the second cuff substrate 206. The fold 274 formed by the folding roll 266 may be pulled to the surface 280 of the vacuum roll 278 by the vacuum force F. Thus, the fold 274 may be substantially planar with the leading edge portion 192 and the trailing edge portion 194, as illustrated in FIG. 10B. The vacuum force F may hold the fold 274 and the leading edge portion 192 of the discrete barrier member 190 in position as the first cuff substrate 204, the second cuff substrate 206, and the discrete barrier member 190 are advanced to the topsheet substrate 286.

Figure 11:
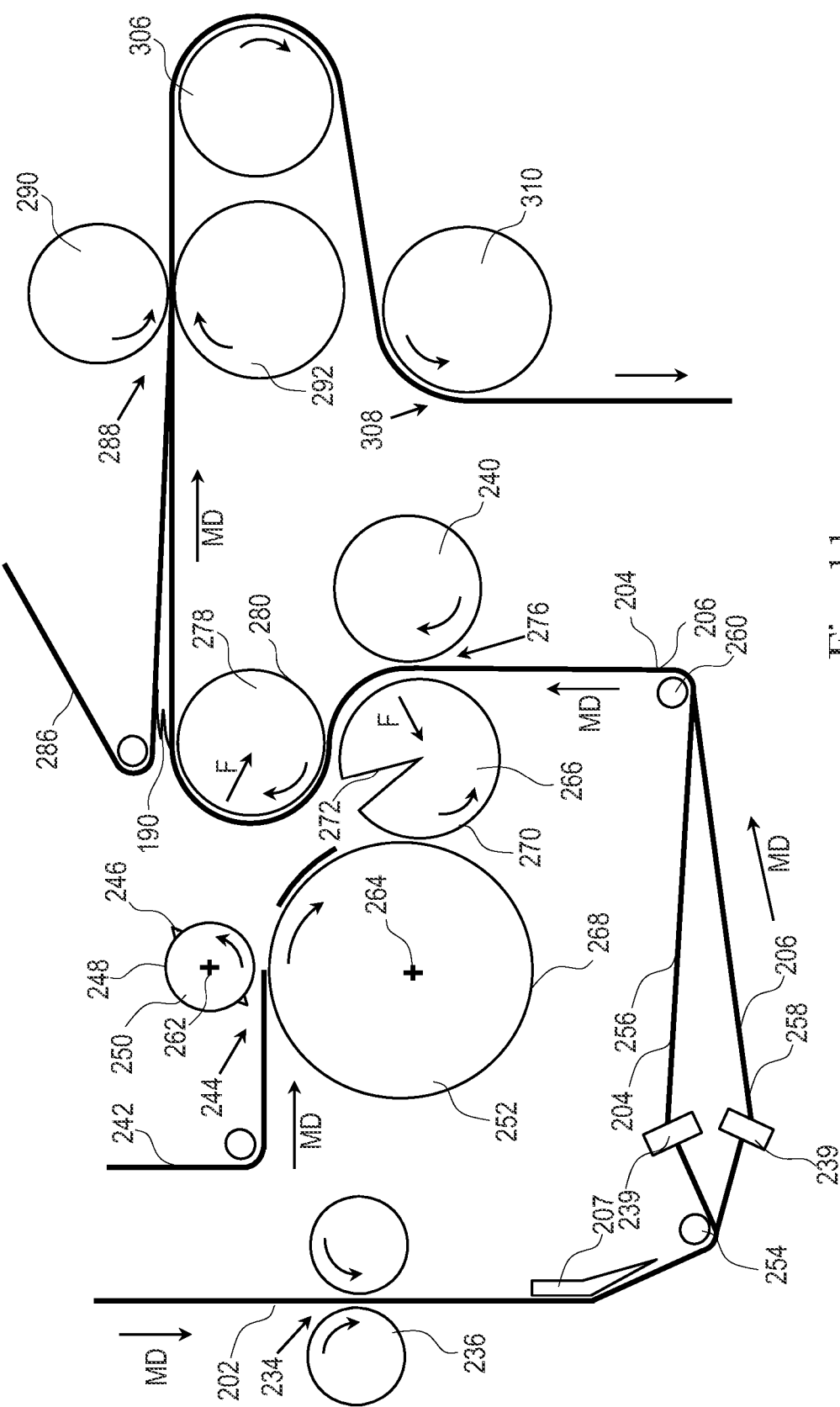
FIG. 11 is a schematic representation of a process used to manufacture absorbent articles comprising a discrete barrier member in accordance with one non-limiting embodiment of the present disclosure.
Figure 12:
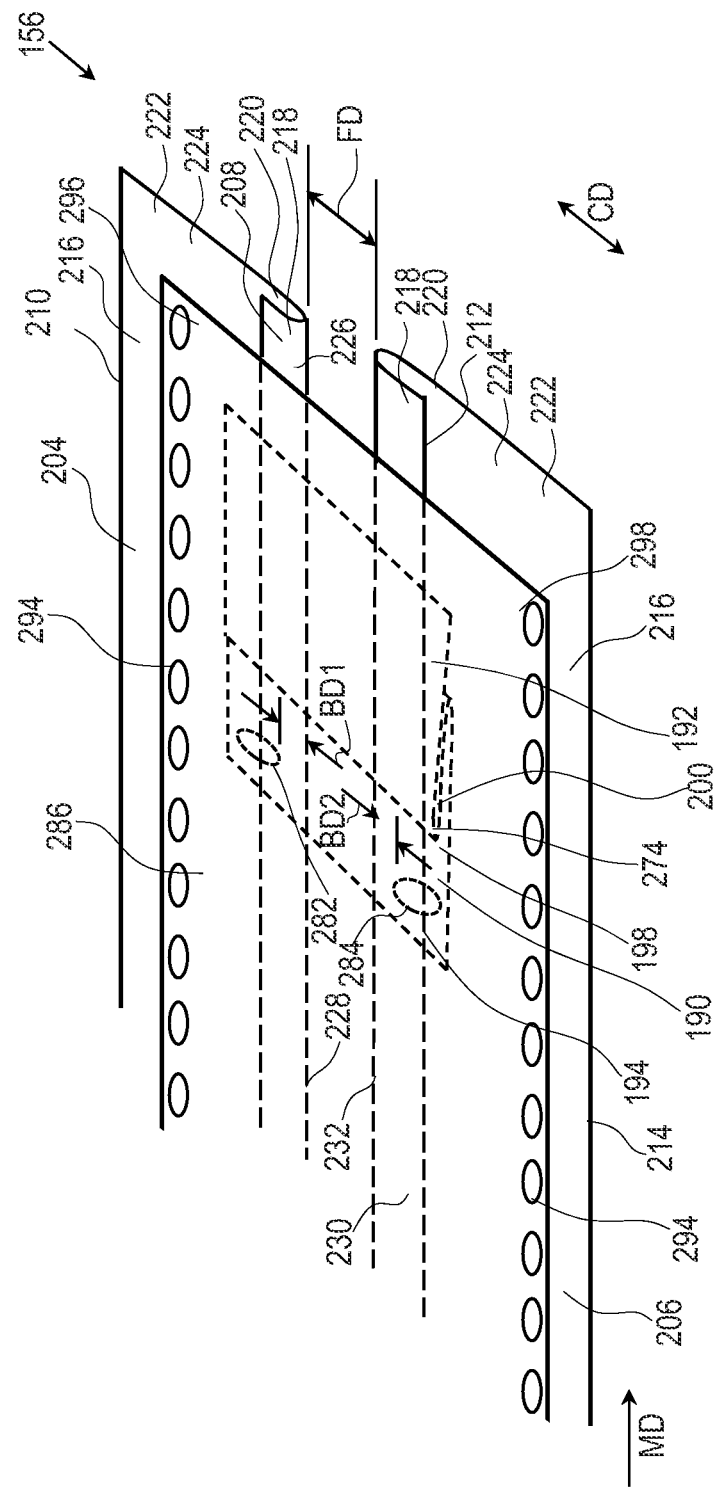
FIG. 12 is a perspective view of a topsheet substrate disposed on a discrete barrier member, and a portion of the first cuff substrate and the second cuff substrate in accordance with one non-limiting embodiment of the present disclosure.

As illustrated in FIGS. 11 and 12, a topsheet substrate 286 may be disposed on at least a portion of the first surface 198 of the discrete barrier member 190. In some exemplary embodiments, the topsheet substrate 286 may substantially cover the discrete barrier member 190. Further, the topsheet substrate 286 may be disposed on at least a portion of the first cuff substrate 204 and the second cuff substrate 206. Thus, the discrete barrier member 190 may be positioned between the topsheet substrate 286 and the first and second cuff substrates 204, 206. The topsheet substrate 286 disposed on the discrete barrier member 190 and at least a portion of the first cuff substrate 204 and the second cuff substrate 206 may be advanced to a second bonding area 288. The second boding area 288 may connect the topsheet substrate 286 to at least a portion of the first cuff substrate 204 and the second cuff substrate 206. The second bonding area 288 may include a second bond roll 290 and a third bond roll 292. The second bond roll 290 may operatively engage the third bond roll 292 to form a linear bond 294 between the topsheet substrate 286 and the first cuff substrate 204 and the topsheet substrate 286 and the second cuff substrate 206, as illustrated in FIG. 12. More specifically, the topsheet substrate 286 may be bonded to at least one of the first cuff surface 216 and the second cuff surface 218 of each of the first cuff substrate 204 and the second cuff substrate 206. For example, in some embodiments, the topsheet substrate 286 may be bonded to the first cuff surface 216 of each of the first cuff substrate 204 and the second cuff substrate 206. The linear bond 294 may extend longitudinally in the machine direction MD on at least one of the first cuff surface 216 and the second cuff surface 218 of each of the first cuff substrate 204 and the second cuff substrate 206, as illustrated in FIG. 12. The bond may be made by, for example, high pressure welding, hot air welding, heat crimping, or ultrasonic welding. Exemplary bonding methods and apparatuses may include those described in U.S. Pat. Nos. 4,854,984; 4,919,738; 5,711,847; 5,817,199; 6,123,792; 7,449,084; 6,248,195; 6,546,987; and U.S. patent application Ser. Nos. 14/038,812; 61/836,690; and 61/836,745.

Figure 13A:
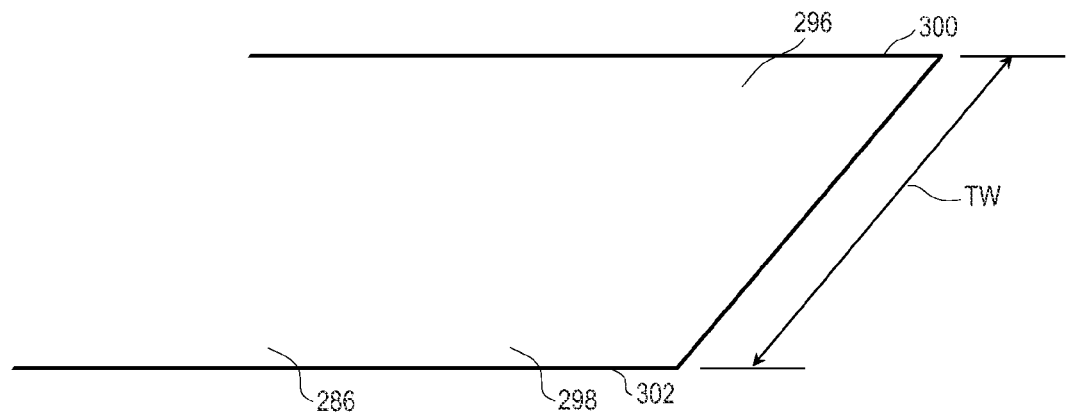
FIG. 13A is a perspective view of a topsheet substrate in accordance with one non-limiting embodiment of the present disclosure.

As previously discussed, the first cuff substrate 204 may be a first distance FD away from the second cuff substrate 206. Having the cuff separated by a first distance may allow the discrete barrier member 190 to be bonded to the first cuff substrate 204 and the second cuff substrate 206 in a relaxed or unstretched state. However, in some embodiments, having the first cuff substrate 204 being separated by a first distance FD from the second cuff substrate 206 when the topsheet substrate 286 is disposed on the discrete barrier member 190, the first cuff substrate 204, and the second cuff substrate 206 may create a problem. More specifically, the topsheet substrate 286 may have a topsheet width TW, a first topsheet edge region 296, a second topsheet edge region 298 opposite the first topsheet edge region 298, a first topsheet edge 300, and a second topsheet edge opposite the first topsheet edge, as illustrated in FIG. 13A. If the first cuff substrate 204 and the second cuff substrate are separated by a first distance FD, the topsheet width TW may position each of the first topsheet edge region 296 and the second topsheet edge region 298 too far away from the first fold edge 228 and the second fold edge 232, respectively, for the linear bond 294 to be positioned in the desired location. Stated another way, in some exemplary embodiments, the topsheet substrate 286 may be positioned with respect to the first cuff substrate 204 such that at least one of the first fold edge 230 and the first inner cuff edge 208 are at a distance from about 15 mm to about 45 mm and/or about 20 mm to about 35 mm and/or about 25 mm to about 32 mm to the first topsheet edge 300. Similarly, the topsheet substrate 286 may be positioned with respect to the second cuff substrate 206 such that at least one of the second fold edge 232 and the second inner cuff edge 212 are at a distance from about 15 mm to about 45 mm and/or about 20 mm to about 35 mm and/or about 25 mm to about 32 mm to the second topsheet edge 302.

Figure 13B:
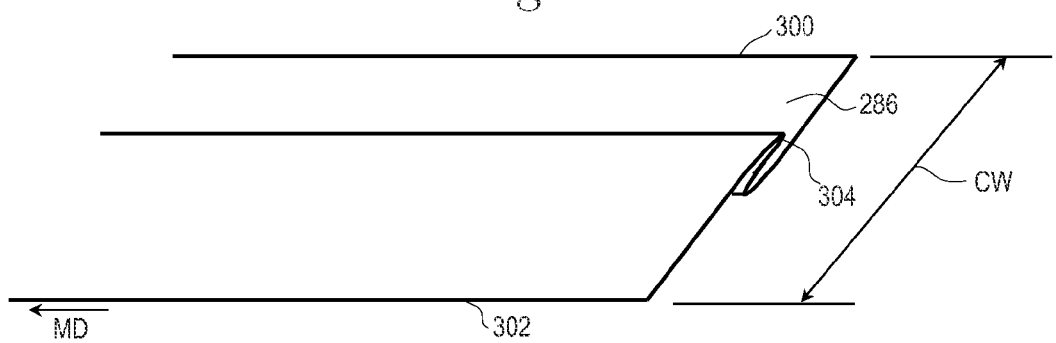
FIG. 13B is a perspective view of a topsheet substrate having a compressed topsheet width in accordance with one non-limiting embodiment of the present disclosure.

Therefore, when the position of the first cuff substrate 204 and the second cuff substrate 206 do not allow the topsheet substrate 286 to be disposed in the proper position for bonding, the topsheet substrate 286 may be manipulated prior to being disposed on the first cuff substrate 204, the second cuff substrate 206, and the discrete barrier member 190. For instance, the topsheet substrate 286 may be manipulated to include a topsheet fold 304, as illustrate in FIG. 13B. The topsheet fold 304 may be substantially parallel to at least one of the first topsheet edge 300 and the second topsheet edge 302. The topsheet fold 304 may extend in the machine direction MD. The topsheet fold 304 may form a compressed topsheet width CW that is less than the topsheet width TW. It is to be appreciated that the number of topsheet folds 304 and/or the width of the topsheet fold may depend on the first distance FD between the first cuff substrate 204 and the second cuff substrate 206.

Figure 13C:
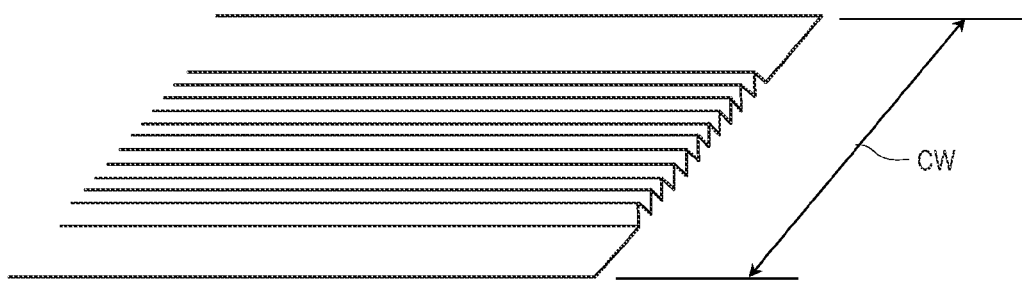
FIG. 13C is a perspective view of a topsheet substrate having a compressed topsheet width in accordance with one non-limiting embodiment of the present disclosure.

In some exemplary embodiments, the topsheet substrate 286 may undergo mechanical activation to form a topsheet substrate having a compressed topsheet width CW and to impart extensibility in at least one of the lateral direction and the longitudinal direction of the topsheet substrate 286. Exemplary mechanical activation methods and apparatuses may include those described in U.S. Pat. Nos. 6,632,504; 5,916,661; 5,628,097, and U.S. Patent Publication No. 2003/0021651, and U.S. patent application Ser. Nos. 14/032,595; 14/247,276; and 14/270,468. The mechanical activation of the topsheet substrate 286 may result in the topsheet substrate 286 having a compressed topsheet width CW that is less than the topsheet width TW, as illustrated in FIG. 13C. It is to be appreciated that the type and amount of mechanical activation may depend on the first distance FD between the first cuff substrate 204 and the second cuff substrate 206. It is also to be appreciated that any number of methods to reduce the width of the topsheet substrate may to be used so that the topsheet substrate 286 may be appropriately positioned on the first cuff substrate 204 and the second cuff substrate 206. For example, a topsheet substrate 286 may undergo folding and mechanical activation to reduce to topsheet width TW to the compressed topsheet width CW.

Figure 14:
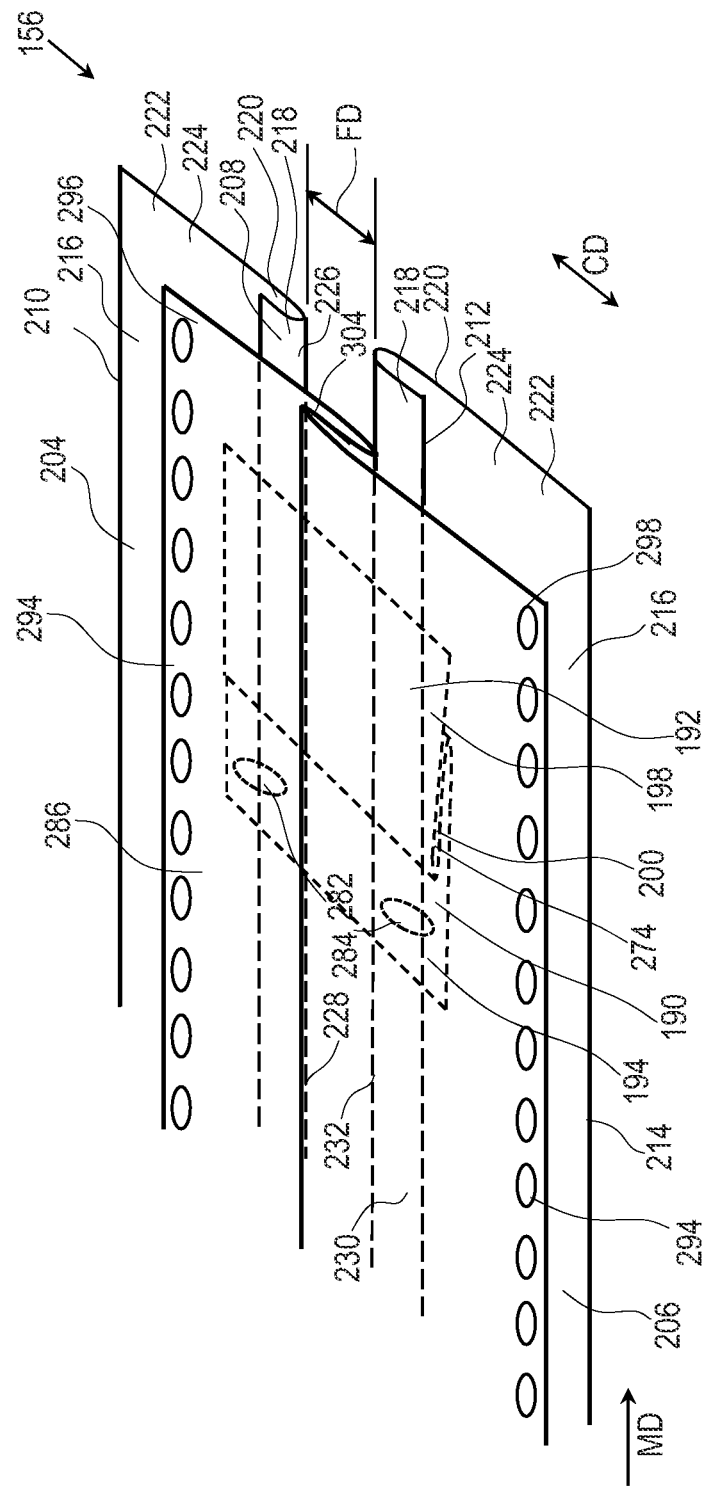
FIG. 14 is a perspective view of a topsheet substrate disposed on a discrete barrier member, and a portion of the first cuff substrate and the second cuff substrate in accordance with one non-limiting embodiment of the present disclosure.

FIG. 14 illustrates a topsheet substrate 286 having a compressed topsheet width CW disposed on the first cuff substrate 204, the second cuff substrate 206, and the discrete barrier member 190. The compressed topsheet width CW may allow the topsheet substrate 286 to be disposed on the first cuff substrate 204 and the second cuff substrate 206 such that the topsheet substrate 286 may be in the desired position to be connected to the first and second cuff substrates 204, 206.

It is to be appreciated that the first cuff substrate 204 and the second cuff substrate 206 may be separated by a distance such that the topsheet width TW does not need to be reduced to the compressed topsheet width CW, and the topsheet substrate 286 can be disposed on the first cuff substrate 204 and the second cuff substrate 206 without any prior manipulation, such as folding, as illustrated in FIG. 12. Assuming that the first cuff substrate 204 and the second cuff substrate 206 are separated by a distance that allows for the topsheet substrate 286 to be positioned without prior manipulation, the topsheet substrate 286 may be advanced to a fourth bonding roll 310. At the fourth bonding roll 310, the topsheet substrate 286 may be bonded to the discrete barrier member 190, the first cuff substrate 204, and the second cuff substrate 206, as will be discussed in more detail below.

Figure 15:
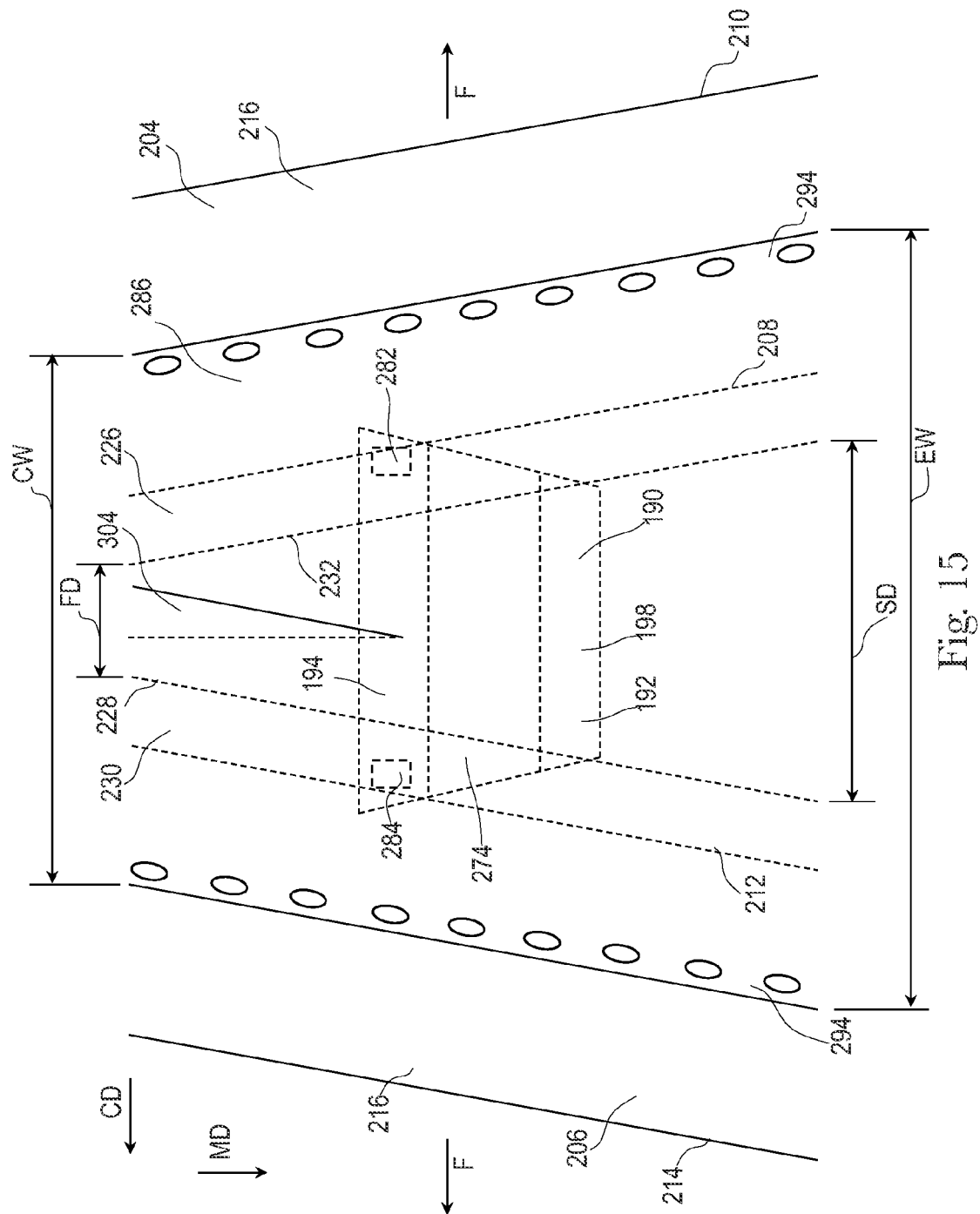
FIG. 15 is a top view of a topsheet substrate disposed on a discrete barrier member, and a portion of the first cuff substrate and the second cuff substrate in accordance with one non-limiting embodiment of the present disclosure.

Assuming that the first cuff substrate 204 and the second cuff substrate 206 are separated by a first distance FD and the topsheet substrate 286 is disposed on the first cuff substrate 204 and the second cuff substrate 206 with a compressed topsheet width CW, as illustrated in FIG. 14, this assembly may be advanced to a separation roll 306, as illustrated in FIG. 11. The separation roll 306 may separate the first cuff substrate 204 from the second cuff substrate 206 and extend, also referring to herein as stretch, the topsheet substrate 286 and the discrete barrier member 190, as illustrated in FIG. 15. A force F may be applied to the first cuff substrate 204 and the second cuff substrate 206 to separate the first cuff substrate 204 from the second cuff substrate 206 and to extend the topsheet substrate 286 and the discrete barrier member 190. More specifically, the force F acts in a direction substantially perpendicular to the machine direction MD, as shown in FIG. 15. During the time the force F acts on each cuff substrate, the linear bond 294 between each of the first cuff substrate 204 and the second cuff substrate 206 and the topsheet substrate 286 continues to connect the topsheet substrate 286 to each cuff substrate 204, 206. Similarly, the bond between the trailing edge portion 194 and the first and second cuff substrates 204, 206 also remains connected during the separation of the cuff substrates. Thus, in some embodiments, the linear bond 294 may be strong enough to withstand a greater than 60% and/or greater than 75% and/or greater than 100% and/or greater than 130% elongation in the width of the topsheet substrate 286. The first bond site 282 and the second bond site 284 may be strong enough to withstand a greater than 105% and/or greater than 125% and/or greater than 200% and/or greater than 250% elongation in the width, parallel to the cross direction, of the discrete barrier member 190.

Figure 16:
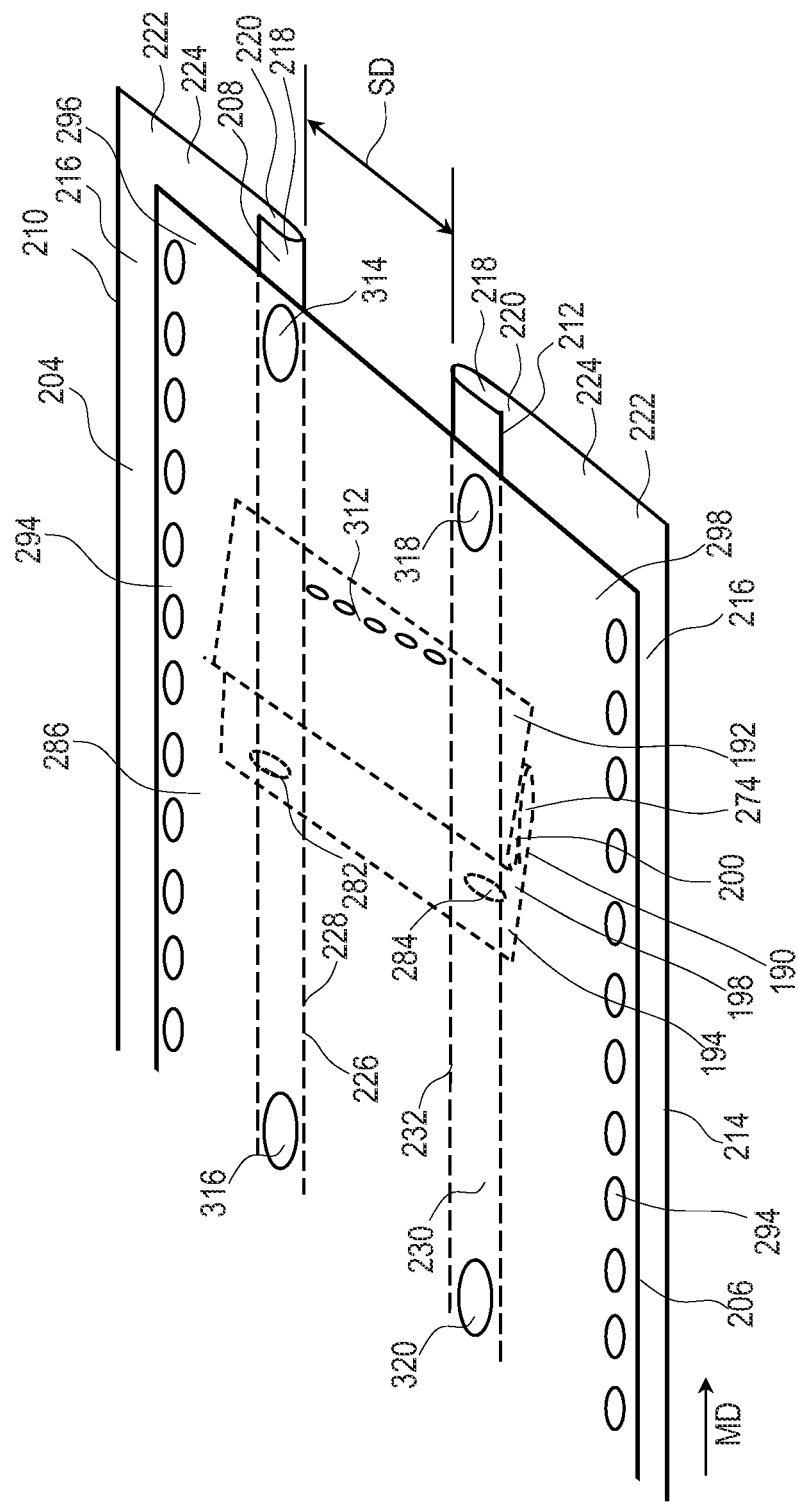
FIG. 16 is a perspective view of a topsheet substrate disposed on a discrete barrier member, and a portion of the first cuff substrate and the second cuff substrate in accordance with one non-limiting embodiment of the present disclosure.

Once fully extended, the first cuff substrate 204 and the second cuff substrate 206 may be separated by a second distance SD, which may be greater than the first distance FD, as illustrated in FIGS. 15 and 16. More specifically, the first fold edge 228 may be separated from a second fold edge 232 by the second distance SD. The second distance SD may be from about 110 mm to about 45 mm and/or from about 96 mm to about 55 mm and/or from about 80 mm to about 64 mm, including all 0.5 mm therebetween. The topsheet substrate 286 may also be extended. The topsheet substrate 286 may be extended by an amount about equal to the second distance SD. Thus, the topsheet substrate 286 may have an extended topsheet width EW in the cross direction between the first topsheet edge and the second topsheet edge. The extended topsheet width EW may be equal to about the compressed topsheet width added to the second distance SD minus the first distance FD, or the distance the first cuff substrate 204 was separated from the second cuff substrate 206. In some embodiments, the extended topsheet width EW may be equal to about the topsheet width TW.

Referring to FIG. 11, the extended topsheet substrate 286, first cuff substrate 204, and second cuff substrate 206 may be advanced to a third bonding area 308. The third bonding area 308 may comprise a fourth bond roll 310. The fourth bond roll 310 may connect the topsheet substrate 286 to the discrete barrier member 190, the first cuff substrate 204, and the second cuff substrate, as illustrated in FIG. 16. More specifically, at least a portion of the leading edge portion 192 of the discrete barrier member 190 may be bonded to a portion of the topsheet substrate 286. The bond between the discrete barrier member 190 and the topsheet substrate 286 may be a linear bond 312. The fourth bond roll 310 may also bond the topsheet substrate 286 to the first cuff substrate 204 and the second cuff substrate 206. The topsheet substrate 286 may be bonded to the first cuff substrate 204 at a first bond area 314 and a second bond area 316. Similarly, the topsheet substrate 286 may be bonded to the second cuff substrate 206 at a third bond area 318 and a fourth bond area 320. The bond between the topsheet substrate 286 and any of the discrete barrier member 190 and the first and second cuff substrate 204, 206 may be by, for example, high pressure welding, hot air welding, heat crimping, or ultrasonic welding. Exemplary bonding methods and apparatuses may include those described in U.S. Pat. Nos. 4,854,984; 4,919,738; 5,711,847; 5,817,199; 6,123,792; 7,449,084; 6,248,195; 6,546,987; and U.S. patent application Ser. Nos. 14/038,812; 61/836,690; and 61/836,745.

Referring to FIG. 11, upon exiting the third bond area 308, the topsheet substrate 286 bonded to the discrete barrier member 190, the first cuff substrate 204, and the second cuff substrate 206 may be advanced to other downstream processes.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A method for manufacturing an absorbent article, wherein the absorbent article comprises a topsheet, a backsheet, a core, a discrete barrier member, a first cuff, and a second cuff, the method comprising the steps of:
   advancing a first cuff substrate and a second cuff substrate in a machine direction, wherein the first cuff substrate comprises a first inner cuff edge and a first outer cuff edge and the second cuff substrate comprises a second inner cuff edge and a second outer cuff edge, and wherein the first inner cuff edge is separated from the second inner cuff edge in a cross direction by a first distance;
   advancing a discrete barrier member in the machine direction, wherein the barrier member comprises a leading edge portion, a trailing edge portion opposite the leading edge portion, and a central portion between the leading edge portion and the trailing edge portion;
   folding the discrete barrier member between the leading edge portion and the trailing edge portion;
   connecting the trailing edge portion of the discrete barrier member with the first cuff substrate and the second cuff substrate;
   extending the trailing edge portion of the discrete barrier member in the cross direction by separating the first cuff substrate and the second cuff substrate such that the first inner cuff edge is separated from the second inner cuff edge in the cross direction by a second distance, wherein the second distance is greater than the first distance;
   advancing a topsheet substrate having a first topsheet edge and a second topsheet edge opposite from the first topsheet edge in the cross direction; and
   connecting the leading edge portion of the discrete barrier member with the topsheet substrate.

2. The method of claim 1, wherein each of the first cuff substrate and the second cuff substrate comprise a first surface and an opposing second surface, wherein the first surface and the second surface comprise a first edge region, an opposing second edge region, and a central region therebetween.

3. The method of claim 2, further comprising the step of folding the first cuff substrate and the second cuff substrate such that the first inner cuff edge is folded to associate with at least one of the first edge region and the central region of the first cuff substrate to form a first fold edge and the second inner cuff edge is folded to associate with at least one of the second edge region and the central region of the second cuff substrate to form a second fold edge.

4. The method of claim 1, wherein the discrete barrier member is extensible in at least one of the machine direction and the cross direction.

5. The method of claim 1, further comprising the step of transferring the discrete barrier member onto a folding roll, wherein the folding roll comprises a first engagement portion, a second engagement portion opposite the first engagement portion, and a groove portion between the first engagement portion and the second engagement portion.

6. The method of claim 1, wherein the step of connecting the trailing edge portion of the discrete barrier member with the first cuff substrate and the second cuff substrate includes bonding the trailing edge portion of the discrete barrier member with the first cuff substrate and the second cuff substrate.

7. The method of claim 6, wherein bonding comprises at least one of high pressure welding, hot air welding, heated crimping, rotary ultrasonic welding.

8. The method of claim 6, wherein the step of bonding the trailing edge portion of the discrete barrier member with the first cuff substrate and the second cuff substrate includes adhering the trailing edge portion of the discrete barrier member with the first cuff substrate and the second cuff substrate.

9. The method of claim 1, further comprising the step of transferring the discrete barrier member, the first cuff substrate, and the second cuff substrate to a vacuum roll.

10. The method of claim 1, wherein the topsheet substrate comprises one or more apertures.

11. The method of claim 1, further comprising the step of activating the topsheet substrate such that the topsheet substrate is extensible in at least one of the machine direction and the cross direction.

12. The method of claim 1, further comprising the step of folding the topsheet substrate to form a topsheet fold extending in the machine direction between the first topsheet edge and the second topsheet edge.

13. The method of claim 1, further comprising the step of positioning the topsheet substrate over at least a portion of the first cuff substrate, the second cuff substrate, and the discrete barrier member.

14. The method of claim 13, wherein the discrete barrier member is positioned between the topsheet substrate and at least one of the first cuff substrate and the second cuff substrate.

15. The method of claim 1, further comprising the step of connecting the topsheet substrate with the first cuff substrate and the second cuff substrate.

16. The method of claim 1, further comprising the step of stretching the topsheet substrate such that the first topsheet edge is separated from the second topsheet edge in the cross direction by an extended topsheet width.

17. A method for manufacturing an absorbent article, wherein the absorbent article comprises a topsheet, a backsheet, a core, a discrete barrier member, a first cuff, and a second cuff, the method comprising the steps of:
- advancing a first cuff substrate and a second cuff substrate in a machine direction, wherein the first cuff substrate comprises a first inner cuff edge and an opposing first outer cuff edge, and wherein the second cuff substrate comprises a second inner cuff edge and an opposing second outer cuff edge, and wherein each of the first cuff substrate and the second cuff substrate comprise a first cuff surface and a second cuff surface that each include an inner edge region, an opposing outer edge region, and a central region therebetween;
- folding the first cuff substrate such that the first inner cuff edge is associated with at least one of the first edge region and the central region of the first cuff surface to form a first cuff fold, wherein the first cuff fold comprises a first fold edge;
- folding the second cuff substrate such that the second inner cuff edge is associated with at least one of the first edge region and the central region of the first cuff surface to form a second cuff fold, wherein the second cuff fold comprises a second fold edge, wherein the first fold edge is separated by the second fold edge by a first distance in a cross direction;
- advancing a discrete barrier member in the machine direction, wherein the barrier member comprises a leading edge portion, a trailing edge portion opposite the leading edge portion, and a central portion between the leading edge portion and the trailing edge portion;
- folding the discreet barrier member between the leading edge portion and the trailing edge portion;
- connecting the trailing edge portion of the discrete barrier member with the first cuff substrate and the second cuff substrate;
- advancing a topsheet substrate having a first topsheet edge opposite from the second topsheet edge in the cross direction, wherein the first topsheet edge and the second topsheet edge extend longitudinally in the machine direction; and
- connecting the leading edge portion of the discrete barrier member with the topsheet substrate.

18. A method for manufacturing an absorbent article, wherein the absorbent article comprises a topsheet, a backsheet, a core, a discrete barrier member, a first cuff, and a second cuff, the method comprising the steps of:
- cutting a barrier substrate into a discrete barrier member comprising a leading edge portion, an opposing trailing edge portion, and a central portion therebetween;
- transferring the discrete barrier substrate onto a folding roll;
- advancing a first cuff substrate and a second cuff substrate onto the folding roll such that the discrete barrier substrate is disposed on at least a portion of the first cuff substrate and the second cuff substrate;
- connecting the trailing edge portion of the discrete barrier member with the first cuff substrate and the second cuff substrate;
- folding the discrete barrier member between the leading edge portion and the trailing edge portion;
- associating a topsheet substrate with at least a portion of the discrete barrier member, the first cuff substrate, and the second cuff substrate; and
- connecting the leading edge portion of the discrete barrier member with the topsheet substrate.

19. The method of claim 18, further comprising the step of stretching the trailing edge portion of the discrete barrier member by separating the first cuff substrate and the second cuff substrate in the cross direction.

20. The method of claim 18, further comprising the step of folding the first cuff substrate and the second cuff substrate to form a first cuff fold and a second cuff fold.

* * * * *